US012465419B2

(12) United States Patent
Roomi

(10) Patent No.: US 12,465,419 B2
(45) Date of Patent: Nov. 11, 2025

(54) ROTATION ASSEMBLY FOR ENERGY-BASED SURGICAL INSTRUMENTS

(71) Applicant: Covidien LP, Mansfield, MA (US)

(72) Inventor: Amir Roomi, Boulder, CO (US)

(73) Assignee: Covidien LP, Mansfield, MA (US)

( * ) Notice: Subject to any disclaimer, the term of this patent is extended or adjusted under 35 U.S.C. 154(b) by 803 days.

(21) Appl. No.: 17/521,694

(22) Filed: Nov. 8, 2021

(65) Prior Publication Data

US 2022/0183743 A1 Jun. 16, 2022

Related U.S. Application Data

(63) Continuation-in-part of application No. 17/122,062, filed on Dec. 15, 2020, now Pat. No. 11,806,068.

(51) Int. Cl.
*A61B 18/14* (2006.01)
*A61B 18/00* (2006.01)

(52) U.S. Cl.
CPC .. *A61B 18/149* (2013.01); *A61B 2018/00178* (2013.01); *A61B 2018/00202* (2013.01)

(58) Field of Classification Search
CPC .............. A61B 18/1445; A61B 18/149; A61B 2017/2929; A61B 2018/00178; A61B 2018/00202; A61B 2018/1455
USPC ...................................................... 606/51–52
See application file for complete search history.

(56) References Cited

U.S. PATENT DOCUMENTS

| | | | |
|---|---|---|---|
| 3,100,489 | A | 8/1963 | Bagley |
| D249,549 | S | 9/1978 | Pike |
| D263,020 | S | 2/1982 | Rau, III |
| 4,461,297 | A | 7/1984 | Sutter |
| 4,461,305 | A | 7/1984 | Cibley |
| D295,893 | S | 5/1988 | Sharkany et al. |
| D295,894 | S | 5/1988 | Sharkany et al. |
| D298,353 | S | 11/1988 | Manno |
| D299,413 | S | 1/1989 | DeCarolis |
| 5,122,139 | A | 6/1992 | Sutter |
| 5,201,743 | A | 4/1993 | Haber et al. |
| 5,211,655 | A | 5/1993 | Hasson |

(Continued)

OTHER PUBLICATIONS

International Search Report and Written Opinion issued in corresponding International Application No. PCT/US2021/063323 dated Mar. 31, 2022, 15 pages.

(Continued)

*Primary Examiner* — Khadijeh A Vahdat

(57) ABSTRACT

A surgical instrument includes a movable handle movable relative a housing to manipulate an end effector assembly, and a rotation assembly. The rotation assembly includes first and second bodies, where one of the bodies is fixedly disposed within a housing and the other body is rotatably disposed within the housing and fixedly disposed about a shaft. An inner contact ring is fixedly disposed on the first body and includes a first electrical connector. An outer contact ring is fixedly disposed on the first body and includes a second electrical connector. First and second spring contacts maintain electrical contact with the inner and outer contact rings. Each of the first and second spring contacts include a substructure that includes a brush holder, an extension, an electrical connector, and a spring that biases the brush towards the inner or outer contact ring to maintain electrical contact.

16 Claims, 28 Drawing Sheets

(56) References Cited

U.S. PATENT DOCUMENTS

| | | | |
|---|---|---|---|
| 5,254,117 | A | 10/1993 | Rigby et al. |
| D343,453 | S | 1/1994 | Noda |
| D348,930 | S | 7/1994 | Olson |
| D349,341 | S | 8/1994 | Lichtman et al. |
| D354,564 | S | 1/1995 | Medema |
| 5,383,875 | A | 1/1995 | Bays et al. |
| D358,887 | S | 5/1995 | Feinberg |
| 5,454,827 | A | 10/1995 | Aust et al. |
| 5,478,351 | A | 12/1995 | Meade et al. |
| 5,512,721 | A | 4/1996 | Young et al. |
| 5,601,601 | A | 2/1997 | Tal et al. |
| D384,413 | S | 9/1997 | Zlock et al. |
| 5,746,739 | A | 5/1998 | Sutter |
| H1745 | H | 8/1998 | Paraschac |
| D402,028 | S | 12/1998 | Grimm et al. |
| 5,849,022 | A | 12/1998 | Sakashita et al. |
| D408,018 | S | 4/1999 | McNaughton |
| 5,891,140 | A | 4/1999 | Ginn et al. |
| 5,891,142 | A | 4/1999 | Eggers et al. |
| 5,954,736 | A | 9/1999 | Bishop et al. |
| D416,089 | S | 11/1999 | Barton et al. |
| 6,010,516 | A | 1/2000 | Hulka |
| D424,694 | S | 5/2000 | Tetzlaff et al. |
| D425,201 | S | 5/2000 | Tetzlaff et al. |
| 6,106,542 | A | 8/2000 | Toybin et al. |
| 6,117,158 | A | 9/2000 | Measamer et al. |
| H1904 | H | 10/2000 | Yates et al. |
| D449,886 | S | 10/2001 | Tetzlaff et al. |
| D453,923 | S | 2/2002 | Olson |
| D454,951 | S | 3/2002 | Bon |
| D457,958 | S | 5/2002 | Dycus et al. |
| D457,959 | S | 5/2002 | Tetzlaff et al. |
| H2037 | H | 7/2002 | Yates et al. |
| D465,281 | S | 11/2002 | Lang |
| D466,209 | S | 11/2002 | Bon |
| D493,888 | S | 8/2004 | Reschke |
| D496,997 | S | 10/2004 | Dycus et al. |
| D499,181 | S | 11/2004 | Dycus et al. |
| D502,994 | S | 3/2005 | Blake, III |
| D509,297 | S | 9/2005 | Wells |
| D525,361 | S | 7/2006 | Hushka |
| 7,083,613 | B2 | 8/2006 | Treat |
| D531,311 | S | 10/2006 | Guerra et al. |
| D533,274 | S | 12/2006 | Visconti et al. |
| D533,942 | S | 12/2006 | Kerr et al. |
| D535,027 | S | 1/2007 | James et al. |
| 7,166,106 | B2 | 1/2007 | Bartel et al. |
| D538,932 | S | 3/2007 | Malik |
| D541,418 | S | 4/2007 | Schechter et al. |
| D541,611 | S | 5/2007 | Aglassinge |
| D541,938 | S | 5/2007 | Kerr et al. |
| 7,211,079 | B2 | 5/2007 | Treat |
| D545,432 | S | 6/2007 | Watanabe |
| D547,154 | S | 7/2007 | Lee |
| D564,662 | S | 3/2008 | Moses et al. |
| D567,943 | S | 4/2008 | Moses et al. |
| D575,395 | S | 8/2008 | Hushka |
| D575,401 | S | 8/2008 | Hixson et al. |
| D582,038 | S | 12/2008 | Swoyer et al. |
| 7,628,791 | B2 | 12/2009 | Garrison et al. |
| D617,900 | S | 6/2010 | Kingsley et al. |
| D617,901 | S | 6/2010 | Unger et al. |
| D617,902 | S | 6/2010 | Twomey et al. |
| D617,903 | S | 6/2010 | Unger et al. |
| D618,798 | S | 6/2010 | Olson et al. |
| D621,503 | S | 8/2010 | Otten et al. |
| D627,462 | S | 11/2010 | Kingsley |
| D628,289 | S | 11/2010 | Romero |
| D628,290 | S | 11/2010 | Romero |
| D630,324 | S | 1/2011 | Reschke |
| 7,922,718 | B2 | 4/2011 | Moses et al. |
| D649,249 | S | 11/2011 | Guerra |
| D649,643 | S | 11/2011 | Allen, IV et al. |
| 8,152,806 | B2 | 4/2012 | Black et al. |
| D661,394 | S | 6/2012 | Romero et al. |
| 8,728,118 | B2 | 5/2014 | Hinman et al. |
| 8,747,434 | B2 | 6/2014 | Larson et al. |
| 8,814,865 | B2 | 8/2014 | Reschke |
| 8,939,973 | B2 | 1/2015 | Garrison et al. |
| 8,945,126 | B2 | 2/2015 | Garrison et al. |
| 8,945,127 | B2 | 2/2015 | Garrison et al. |
| 9,089,327 | B2 | 7/2015 | Worrell et al. |
| 9,101,385 | B2 | 8/2015 | Shelton, IV et al. |
| 9,113,907 | B2 | 8/2015 | Allen, IV et al. |
| 9,113,937 | B2 | 8/2015 | Collings et al. |
| 9,113,940 | B2 | 8/2015 | Twomey |
| 9,124,013 | B2 | 9/2015 | Frushhour et al. |
| 9,241,728 | B2 | 1/2016 | Price et al. |
| 9,241,732 | B2 | 1/2016 | Craig |
| 9,259,263 | B2 | 2/2016 | Anderson et al. |
| 9,259,266 | B2 | 2/2016 | Schmaltz et al. |
| 9,265,566 | B2 | 2/2016 | O'Neill et al. |
| 9,265,570 | B2 | 2/2016 | Heard |
| 9,368,004 | B2 | 6/2016 | Plaven |
| 9,370,393 | B2 | 6/2016 | Chojin et al. |
| 9,375,205 | B2 | 6/2016 | Mueller |
| 9,375,227 | B2 | 6/2016 | Garrison et al. |
| 9,375,256 | B2 | 6/2016 | Cunningham et al. |
| 9,375,259 | B2 | 6/2016 | Payne et al. |
| 9,375,260 | B2 | 6/2016 | Kerr |
| 9,375,262 | B2 | 6/2016 | Reschke et al. |
| 9,456,863 | B2 | 10/2016 | Moua |
| 9,468,453 | B2 | 10/2016 | Hart et al. |
| 9,480,522 | B2 | 11/2016 | Horner et al. |
| 9,492,225 | B2 | 11/2016 | Dycus et al. |
| 9,498,281 | B2 | 11/2016 | Kendrick |
| 9,526,564 | B2 | 12/2016 | Rusin |
| 9,549,749 | B2 | 1/2017 | Kendrick |
| 9,549,775 | B2 | 1/2017 | Dumbauld et al. |
| 9,554,845 | B2 | 1/2017 | Arts |
| 9,572,529 | B2 | 2/2017 | Latimer et al. |
| 9,579,145 | B2 | 2/2017 | Johnson et al. |
| 9,608,395 | B2 | 3/2017 | Overweg |
| 9,622,810 | B2 | 4/2017 | Hart et al. |
| 9,649,174 | B2 | 5/2017 | Swarup et al. |
| 9,655,673 | B2 | 5/2017 | McCullough, Jr. et al. |
| 9,844,888 | B2 | 12/2017 | Pesavento et al. |
| 9,901,359 | B2 | 2/2018 | Faller et al. |
| 10,211,586 | B2 | 2/2019 | Adams et al. |
| 10,314,643 | B2 | 6/2019 | Amann et al. |
| 10,317,927 | B2 | 6/2019 | Lamser et al. |
| 10,478,984 | B2 | 11/2019 | Pesavento et al. |
| 10,500,748 | B2 | 12/2019 | Pesavento et al. |
| 10,517,664 | B2 | 12/2019 | Nagtegaal |
| 10,524,852 | B1 | 1/2020 | Cagle et al. |
| 10,610,290 | B2 | 4/2020 | Bjorn-Rasmussen et al. |
| 10,617,465 | B2 | 4/2020 | Nagtegaal et al. |
| 10,631,861 | B2 | 4/2020 | Shelton, IV et al. |
| 10,653,477 | B2 | 5/2020 | Nagtegaal |
| 10,687,886 | B2 | 6/2020 | McCullough, Jr. et al. |
| 2002/0188294 | A1 | 12/2002 | Couture et al. |
| 2003/0018331 | A1 | 1/2003 | Dycus et al. |
| 2003/0109875 | A1 | 6/2003 | Tetzlaff et al. |
| 2003/0171747 | A1 | 9/2003 | Kanehira et al. |
| 2003/0229344 | A1 | 12/2003 | Dycus et al. |
| 2004/0082952 | A1 | 4/2004 | Dycus et al. |
| 2004/0116952 | A1 | 6/2004 | Sakurai et al. |
| 2004/0176762 | A1 | 9/2004 | Lawes et al. |
| 2004/0243125 | A1 | 12/2004 | Dycus et al. |
| 2005/0154387 | A1 | 7/2005 | Moses et al. |
| 2007/0260241 | A1 | 11/2007 | Dalla Betta et al. |
| 2008/0009860 | A1 | 1/2008 | Odom |
| 2008/0114349 | A1 | 5/2008 | Treat |
| 2008/0215048 | A1 | 9/2008 | Hafner et al. |
| 2008/0262491 | A1 | 10/2008 | Swoyer et al. |
| 2009/0088792 | A1 | 4/2009 | Hoell, Jr. et al. |
| 2010/0030205 | A1 | 2/2010 | Herzon |
| 2010/0179540 | A1 | 7/2010 | Marczyk et al. |
| 2011/0184459 | A1 | 7/2011 | Malkowski et al. |
| 2011/0190765 | A1 | 8/2011 | Chojin |
| 2011/0251613 | A1 | 10/2011 | Guerra et al. |
| 2011/0301592 | A1 | 12/2011 | Kerr et al. |
| 2011/0301603 | A1 | 12/2011 | Kerr et al. |
| 2012/0022524 | A1 | 1/2012 | Timm et al. |

(56) References Cited

U.S. PATENT DOCUMENTS

| | | | |
|---|---|---|---|
| 2012/0022529 A1 | 1/2012 | Shelton, IV et al. | |
| 2012/0109186 A1 | 5/2012 | Parrott et al. | |
| 2012/0136347 A1 | 5/2012 | Brustad et al. | |
| 2013/0018411 A1 | 1/2013 | Collings et al. | |
| 2013/0325057 A1 | 12/2013 | Larson et al. | |
| 2014/0094798 A1 | 4/2014 | Garrison et al. | |
| 2014/0100564 A1 | 4/2014 | Garrison | |
| 2014/0100568 A1 | 4/2014 | Garrison | |
| 2014/0100569 A1 | 4/2014 | Lawes et al. | |
| 2014/0107443 A1 | 4/2014 | Hoarau et al. | |
| 2014/0107648 A1 | 4/2014 | Harper et al. | |
| 2014/0121507 A1 | 5/2014 | Nau, Jr. | |
| 2014/0135763 A1 | 5/2014 | Kappus et al. | |
| 2014/0194875 A1 | 7/2014 | Reschke et al. | |
| 2014/0221994 A1 | 8/2014 | Reschke | |
| 2014/0230243 A1 | 8/2014 | Roy et al. | |
| 2014/0236149 A1 | 8/2014 | Kharin et al. | |
| 2014/0257284 A1 | 9/2014 | Artale | |
| 2014/0276803 A1 | 9/2014 | Hart | |
| 2014/0353188 A1 | 12/2014 | Reschke et al. | |
| 2015/0018816 A1 | 1/2015 | Latimer | |
| 2015/0133993 A1 | 5/2015 | Twomey | |
| 2016/0121143 A1* | 5/2016 | Mumaw | A61B 90/08 601/2 |
| 2017/0281218 A1* | 10/2017 | Timm | A61B 17/320092 |
| 2019/0298437 A1 | 10/2019 | Boone et al. | |
| 2019/0328389 A1 | 10/2019 | Baril et al. | |
| 2020/0305962 A1 | 10/2020 | Ward et al. | |
| 2022/0183744 A1 | 6/2022 | Stamm et al. | |
| 2022/0183745 A1 | 6/2022 | Stamm et al. | |
| 2022/0183746 A1 | 6/2022 | Stamm et al. | |

OTHER PUBLICATIONS

International Preliminary Report on Patentability and Written Opinion issued in corresponding International Application No. PCT/US2021/063323 dated Jun. 29, 2023, 8 pages.

Final Office Action received for U.S. Appl. No. 17/122,062, mailed on Apr. 26, 2023, 13 pages.

Non-Final Office Action received for U.S. Appl. No. 17/122,062, mailed on Jan. 5, 2023, 13 pages.

Non-Final Office Action received for U.S. Appl. No. 17/122,113, mailed on Jul. 3, 2024, 27 pages.

Non-Final Office Action received for U.S. Appl. No. 17/122,113, mailed on Mar. 24, 2023, 22 pages.

Non-Final Office Action received for U.S. Appl. No. 17/122,144, mailed on Apr. 14, 2023, 14 pages.

* cited by examiner

ROTATION ASSEMBLY FOR ENERGY-BASED SURGICAL INSTRUMENTS

CROSS-REFERENCE TO RELATED APPLICATIONS

This application is a continuation-in-part of U.S. patent application Ser. No. 17/122,062, filed on Dec. 15, 2020, now U.S. Pat. No. 11,806,068, the entire contents of which is hereby incorporated herein by reference.

BACKGROUND

Technical Field

The present disclosure relates to rotation assemblies of surgical instruments and, more particularly, to rotation assemblies and energy-based surgical instruments for grasping, treating, and/or dividing tissue incorporating such rotation assemblies.

Background of Related Art

Some energy-based surgical instruments, such as energy-based surgical forceps, utilize mechanical clamping action and application of energy, e.g., radio frequency (RF) energy, ultrasonic energy, microwave energy, light energy, thermal energy, etc., to affect hemostasis by heating tissue to coagulate, cauterize, and/or seal tissue. Coagulation may be sufficient to achieve hemostasis on some tissue, e.g., non-vascular tissue, small blood vessels below about two millimeters in diameter, and tissues including small vessels. However, for other tissue, e.g., large blood vessels above about two millimeters in diameter and tissues including larger vessels, coagulation may be insufficient to achieve hemostasis; instead, these tissues may be required to be sealed, a process by which the collagen in the tissue is heated up, denatured, and reformed into a fused mass to permanently close the vessel(s). Once hemostasis is achieved, the treated tissue may be cut (mechanically, electrically, or electro-mechanically) to divide the tissue.

SUMMARY

As used herein, the term "distal" refers to the portion that is being described which is further from an operator, e.g., a surgeon, while the term "proximal" refers to the portion that is being described which is closer to the operator. Terms including "generally," "about," "substantially," and the like, as utilized herein, are meant to encompass variations, e.g., manufacturing tolerances, material tolerances, use and environmental tolerances, measurement variations, and/or other variations, up to and including plus or minus 10 percent. Further, any or all of the aspects described herein, to the extent consistent, may be used in conjunction with any or all of the other aspects described herein.

Provided in accordance with aspects of the present disclosure is a rotation assembly for a surgical instrument and a surgical instrument including a rotation assembly. The rotation assembly includes first and second bodies, such that one of the first or second bodies is fixedly disposed within the housing of the surgical instrument and defines a central bore that is configured to rotatably receive a shaft of the surgical instrument. The other of the first or second bodies is rotatably disposed within the housing and fixedly disposed about the shaft. The shaft extends distally from the housing and is rotatable relative to the housing. An inner contact ring is fixedly disposed on the first body and includes a first electrical connector coupled thereto. An outer contact ring is fixedly disposed on the first body and includes a second electrical connector coupled thereto, such that the outer contact ring is electrically isolated from the inner contact ring. The first and second spring contacts are configured to maintain electrical contact with the inner and outer contact rings, respectively. Each of the first and second spring contacts includes a substructure, such that the sub-structure includes a brush holder that is positioned towards a first end portion thereof and an extension that is positioned towards a second end portion thereof, an electrical connector disposed on the extension, and a brush that is slidably disposed partially within the brush holder. The brush includes a contact portion that extends from the brush holder and that is configured to establish electrical contact with the inner or outer contact ring. Each of the first and second spring contacts further include a spring that is disposed at least partially within the brush holder, the spring being configured to bias the brush towards the inner or outer contact ring to maintain electrical contact therebetween.

In an aspect of the present disclosure, first body is a continuous rotation assembly and the second body is a rotation wheel of the surgical instrument.

In another aspect of the present disclosure, the rotation assembly further includes a disc disposed within the first body, the disc including: a proximal face, a distal face, and an outer rim.

In yet another aspect of the present disclosure, the distal face is recessed relative to the outer rim.

In still another aspect of the present disclosure, the outer rim is configured for rotatable receipt within a recessed portion of the second body, such that a cavity is formed between the distal face of the disc and the recessed portion of the second body.

In still yet another aspect of the present disclosure, both the inner and outer contact rings are disposed within the cavity.

In another aspect of the present disclosure, the inner contact ring disposed within the cavity is fixed relative to the recessed portion of the second body and fixed relative to the first electrical connector.

In yet another aspect of the present disclosure, the outer contact ring disposed within the cavity is fixed relative to the recessed portion of the second body and fixed relative to the second electrical connector.

In still another aspect of the present disclosure, the rotation assembly further includes a frame defined on the distal face of the disc to surround the central bore and configured to be fixedly captured within the housing.

In still yet another aspect of the present disclosure, the second body is configured to rotate the shaft into a desired orientation, relative to the housing.

In another aspect of the present disclosure, the second body is rotatable continuously in either direction without limitation.

In yet another aspect of the present disclosure, the second body includes a plurality of flutes arranged annularly about an annular periphery thereof.

In still yet another aspect of the present disclosure, the brush is a carbon graphite brush.

In another aspect of the present disclosure, the rotation assembly further includes a distal pair of connector slots disposed in the second body, the distal facing pair of connector slots configured to receive the first and second electrical connectors.

In yet another aspect of the present disclosure, the rotation assembly further includes a proximal pair of connector slots disposed in the first body, the proximal facing pair of connector slots configured to receive a distal pair of electrical connectors.

BRIEF DESCRIPTION OF THE DRAWINGS

The above and other aspects and features of the present disclosure will become more apparent in view of the following detailed description when taken in conjunction with the accompanying drawings wherein like reference numerals identify similar or identical elements.

DETAILED DESCRIPTION

Figure 1:
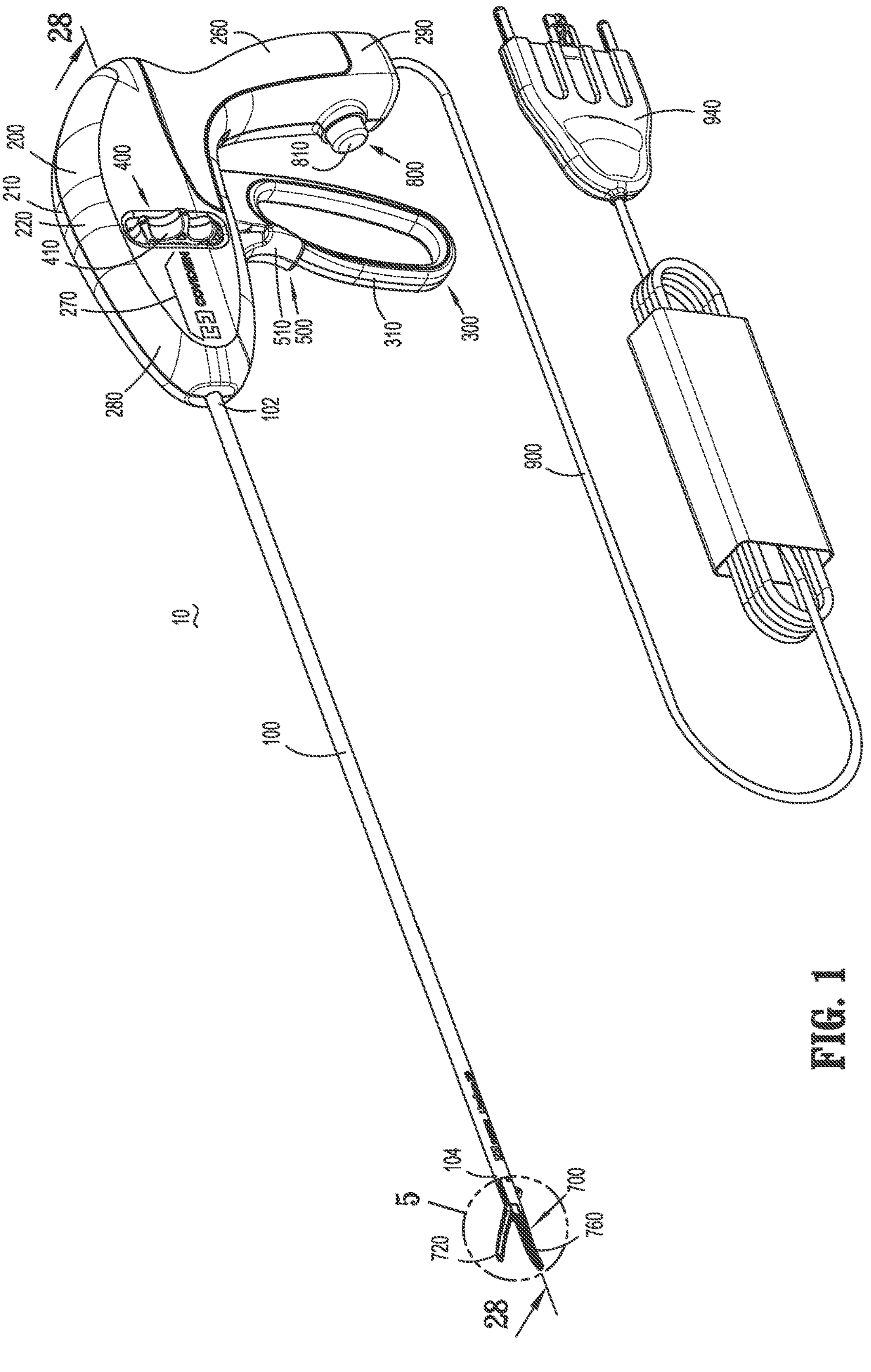
FIG. 1 is a perspective view of an energy-based surgical instrument provided in accordance with the present disclosure.

Referring generally to FIGS. 1-5, an energy-based surgical instrument provided in accordance with the present disclosure and configured for grasping, treating, and/or dividing tissue is shown generally identified by reference numeral 10. Instrument 10 includes a shaft 100, a housing 200, a drive assembly 300, a rotation assembly 400, a trigger assembly 500, a knife assembly 600, an end effector assembly 700, an activation assembly 800, and a cable 900. Cable 900 may be initially wound in an oval-shape configuration for packaging, may be wound to define a figure-eight configuration, or may define any other suitable configuration for packaging.

Shaft 100 extends distally from housing 200 and supports end effector assembly 700 at a distal end portion 104 thereof. More specifically, shaft 100 includes a proximal collar 110 engaged about a proximal end portion 102 thereof that is rotatably secured within housing 200 to rotatably support proximal end portion 102 within housing 200. Proximal end portion 102 of shaft further defines a pair of opposed longitudinally-extending slots 112 and a proximal cut-out 114.

Distal end portion 104 of shaft 100 defines a clevis 120 within which fixed jaw member 760 of end effector assembly 700 is fixedly secured. More specifically, clevis 120 defines weld access apertures 122 through the spaced-apart flags 124, 126 thereof that facilitate laser welding of the spaced-apart flags 766, 768 of proximal flag portion 764 of fixed jaw member 760 to flags 124, 126 of clevis 120, respectively, on the respective interior sides of flags 124, 126 of clevis 120. Other weld locations may additionally or alternatively be provided and/or proximal flag portion 764 of fixed jaw member 760 may be secured within clevis 120 in any other suitable manner. One of the flags 124, 126 of clevis 120, e.g., flag 124 further defines a cut-out 128 (FIG. 5) wherein material extending proximally from a portion of a distal edge of flag 124 and material extending downwardly from an upper edge of flag 124 is removed. However, it is noted that cut-out 128 need not be cut out from the material forming flag 124 after manufacture but, rather, cut-out 128 of flag 124 can be defined upon formation of flag 124. The other flag 126 of clevis 120 defines an angled distal edge 130 that is angled inwardly, e.g., wherein an outer surface of flag 126 extends further distally as compared to an inner surface thereof with angled distal edge 130 interconnecting the outer and inner surfaces of flag 126 (see FIG. 6).

With the exception of weld access apertures 122, the outer surfaces of flags 124, 126 of clevis 120 are smooth and continuous, e.g., without interruption from, for example, cam slots, pivot apertures, etc. Thus, entry of fluids, debris, etc. is inhibited as is catching on or interference by a trocar, other instrument, tissue, debris, etc.

Continuing with reference to FIGS. 1-5, housing 200 of instrument 10 includes first and second housing parts 210, 220, e.g., formed from molding, secured to one another, e.g., via ultrasonic welding, to operably support and/or enclose various components of instrument 10 within housing 200. Housing parts 210, 220, more specifically, may be each be formed from a first shot injection mold and, thereafter, a second shot injection mold may be applied to either or both of housing parts 210, 220 to, for example, define a non-slip grip surface 260. Additionally or alternatively, the second shot injection mold may flow along a runner system defined within either or both housing parts 210, 220 to define internal features such as, for example, wire routing features 234. In some configurations, logos and/or other indicia 270 may be defined as a cut-out through housing part 210 and/or housing part 220 via the first shot injection mold and, then, may be filled with material via the second shot injection mold to provide contrasting color, texture, etc. Thus, the second shot injection mold may define various features associated with housing 200 in a single step, thereby facilitating manufacturing.

Housing parts 210, 220 may either, both, or collectively, define: alignment features 230 (e.g., complementary pegs and apertures, inter-engaging outer edges, etc.) configured to facilitate alignment of housing parts 210, 220 for securement to one another and to maintain alignment thereof; a cable aperture 232 configured to enable passage of cable 900 into housing 200; wire routing features 234 (e.g., guide slots, retention caps, etc.) configured to guide the lead wires 910, 920 from activation assembly 800 to rotation assembly 400 while inhibiting interference thereof with the other operable components within housing 200; an activation button aperture 236 through which activation button 810 of activation assembly 800 protrudes; board support 238 for supporting circuit board 820 of activation assembly 800; a movable handle and trigger slot 240 through which movable handle 310 of drive assembly 300 and trigger 510 of trigger assembly 500 extend from housing 200; opposed rotation wheel windows 242 configured to receive opposed sides of rotation wheel 410 of rotation assembly 400; a distal aperture 244 through which shaft 100 extends distally from housing 200; guide tracks 246 to guide translation of carriage 330 of drive assembly 300; movable handle pivot recesses 248 configured to enable pivotable engagement of movable handle 310 within housing 200; first and second trigger assembly pivot recesses 250, 252 configured to enable pivotable engagement of trigger 510 and linkage 530 of trigger assembly 500 within housing 200; and a partition 254 defining a shaft aperture 256 configured to receive and rotatably support proximal collar 110 and proximal end portion 102 of shaft 100. Housing 200 further includes a body portion 280 and a fixed handle portion 290 depending from body portion 280.

With reference to FIGS. 5-9, end effector assembly 700 is disposed at distal end portion 104 of shaft 100 and includes a movable jaw member 720 and fixed jaw member 760. Jaw members 720, 760 define curved configurations (See FIGS. 5 and 6), although other configurations are also contemplated. Each jaw member 720, 760 includes a structural jaw frame 722, 762, an insulative jaw body 740, 780, and an electrically-conductive plate 750, 790. Each structural jaw frame 722, 762 includes a proximal flag portion 724, 764, respectively, and a distal body portion 725 (only distal body portion 725 of jaw member 720 is shown, the distal body portion of jaw member 760 is similarly configured) extending distally from the respective proximal flag portion 724, 764. Each proximal flag portion 724, 764 includes a pair of spaced-apart flags 726, 728 and 766, 768, respectively. The flags 726, 728 of proximal flag portion 724 of structural jaw frame 722 of jaw member 720 include aligned arcuate cam slots 730 and aligned pivot apertures 732 defined therethrough. The flags 766, 768 of proximal flag portion 764 of structural frame 762 of jaw member 760 include aligned longitudinal cam slots 770 and aligned pivot apertures 772. In an assembled condition of end effector assembly 700, the flags 726, 728 of jaw member 720 are disposed within proximal flag portion 764 of jaw member 760 with each flag 726, 728 disposed adjacent and internally of a corresponding flag 766, 768 of jaw member 760. In this manner, proximal flag portion 724, 764 define a nestled configuration.

A pivot pin 702 is configured to extend through aligned pivot apertures 732, 772 to pivotably couple jaw members 720, 760 with one another, while a cam pin 704 is configured for receipt within cam slots 730, 770 to operably couple jaw members 720, 760 with one another, e.g., such that translation of cam pin 704 through cam slots 730, 770 pivots jaw member 720 relative to jaw member 760. Arcuate cam slots 730 facilitate smooth and consistent pivoting of jaw member 720, e.g., inhibiting binding, while longitudinal cam slots 770 facilitate guiding translation of cam pin 704.

Figure 10:
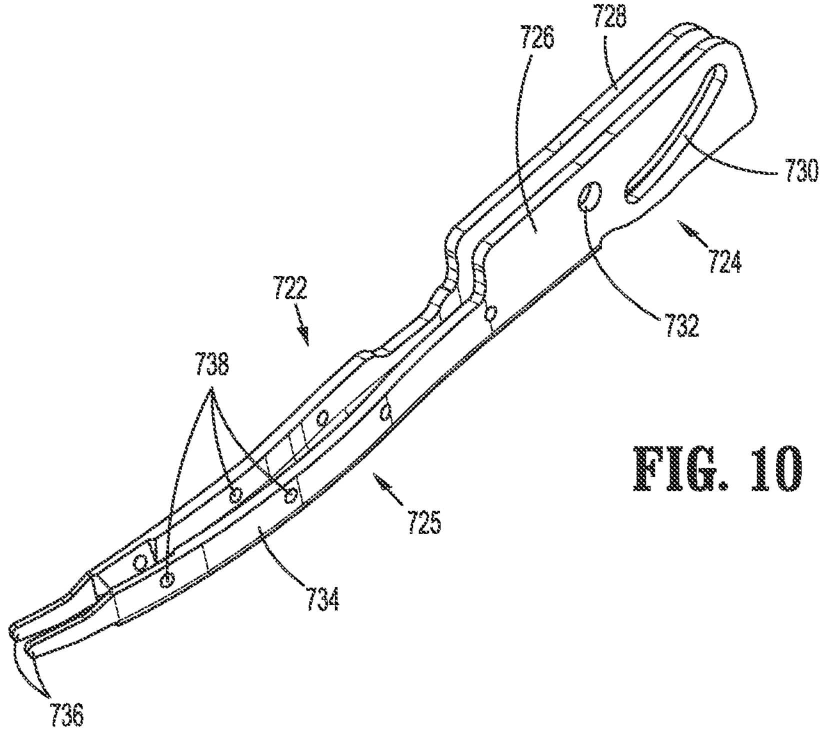
FIG. 10 is a perspective view of a structural jaw frame of one of the jaw members of the instrument of FIG. 1.
Figure 11:
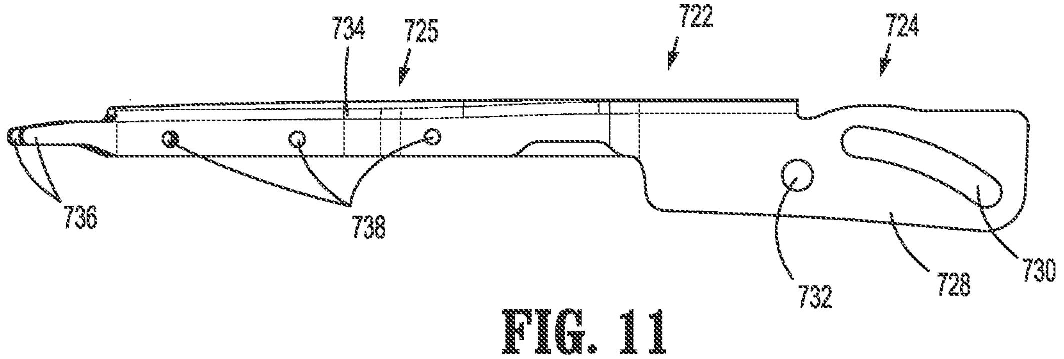
FIG. 11 is a side view of the structural jaw frame of FIG. 10.
Figure 12:
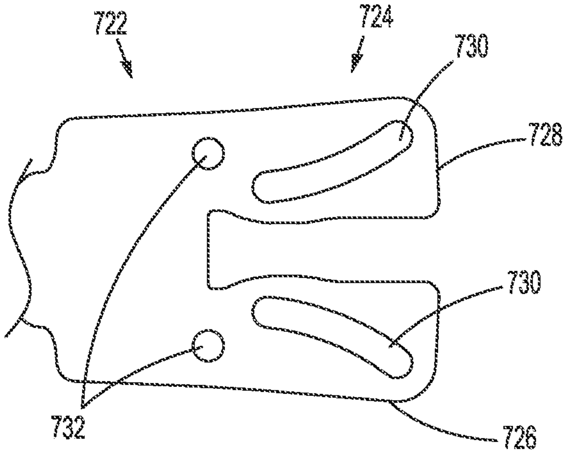
FIG. 12 is a top view of a proximal portion of the structural jaw frame of FIG. 10 in a partially-manufactured condition.

With additional reference to FIGS. 10-12, the distal body portions 725 of structural jaw frames 722, 762 extend distally from the respective proximal flag portions 724, 764. As noted above, only distal body portion 725 of jaw member 720 is shown; the distal body portion of jaw member 760 is similarly configured and, thus, reference herein to distal body portion 725 applies equally to the distal body portion of jaw member 760, except as explicitly contradicted herein. Distal body portion 725, more specifically, define a U-shaped base 734 along the majority of the length thereof; however, distal body portion 725 also includes a pair of spaced-apart fingers 736 extending distally from the distal ends of the uprights of U-shaped base 734. Unlike U-shaped base 734, the spaced-apart fingers 736 are not interconnected by a backspan. The uprights of U-shaped base 734 may include apertures 738 to facilitate overmold retention of insulative jaw body 740 and/or to facilitate manufacture of structural jaw frame 722.

Typically, structural jaw frames are formed via progressive die stamping (or other suitable stamping process), wherein the structural jaw frame is punched from stock material and bent to achieve the desired configuration. Progressive die stamping is advantageous in that it facilitates high volume production. Structural jaw frame 722, however, includes features that make difficult if not inhibit utilization of progressive die stamping. In particular, cam slots 730 extend close to the edge of flags 726, 728, forming thin sections that are not wide enough for die stamping tools, and, likewise, the spacing between flags 726, 728 relative to the height of flags 726, 728 (before bending) is too narrow for die stamping tools. Thus, as an alternative to progressive die stamping, wherein the features are punched into the blank, structural jaw frame 722 may be formed from laser cutting the blanks, wherein structural jaw frame 722 is first cut from sheet stock and/or roller stock using a modulated fiber laser system, e.g., to form cam slots 730 and pivot aperture 732, among other features, and is then fed to tooling to create the additional features, e.g., bends, coins, etc., thereof.

The laser cutting and formation process for manufacturing structural jaw frame 722 may be done in a number of ways such as, for example: the laser cut parts can be singulated, and fed into stage form tooling or transfer tooling (in a manual or automated fashion); the laser cut parts can remain in strips cut to length and fed into stage form tooling, transfer tooling, or progressive tooling (in a manual or automated fashion); or the laser cut parts can remain on a continuous strip and be fed into stage form tooling, transfer tooling, or progressive tooling.

The structural jaw frame 762 of jaw member 760 (FIG. 9) may be formed in a similar manner as structural jaw frame 722 or may be formed via progressive die stamping (or other suitable stamping process).

Figure 6:
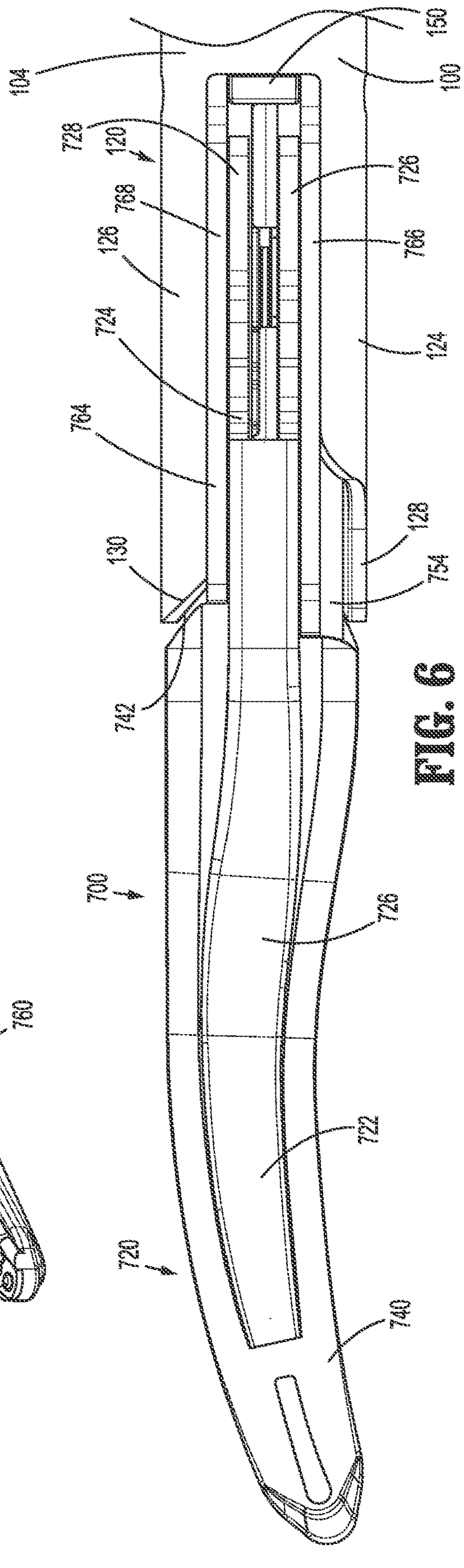
FIG. 6 is a top view of the distal portion of FIG. 5.
Figure 7:
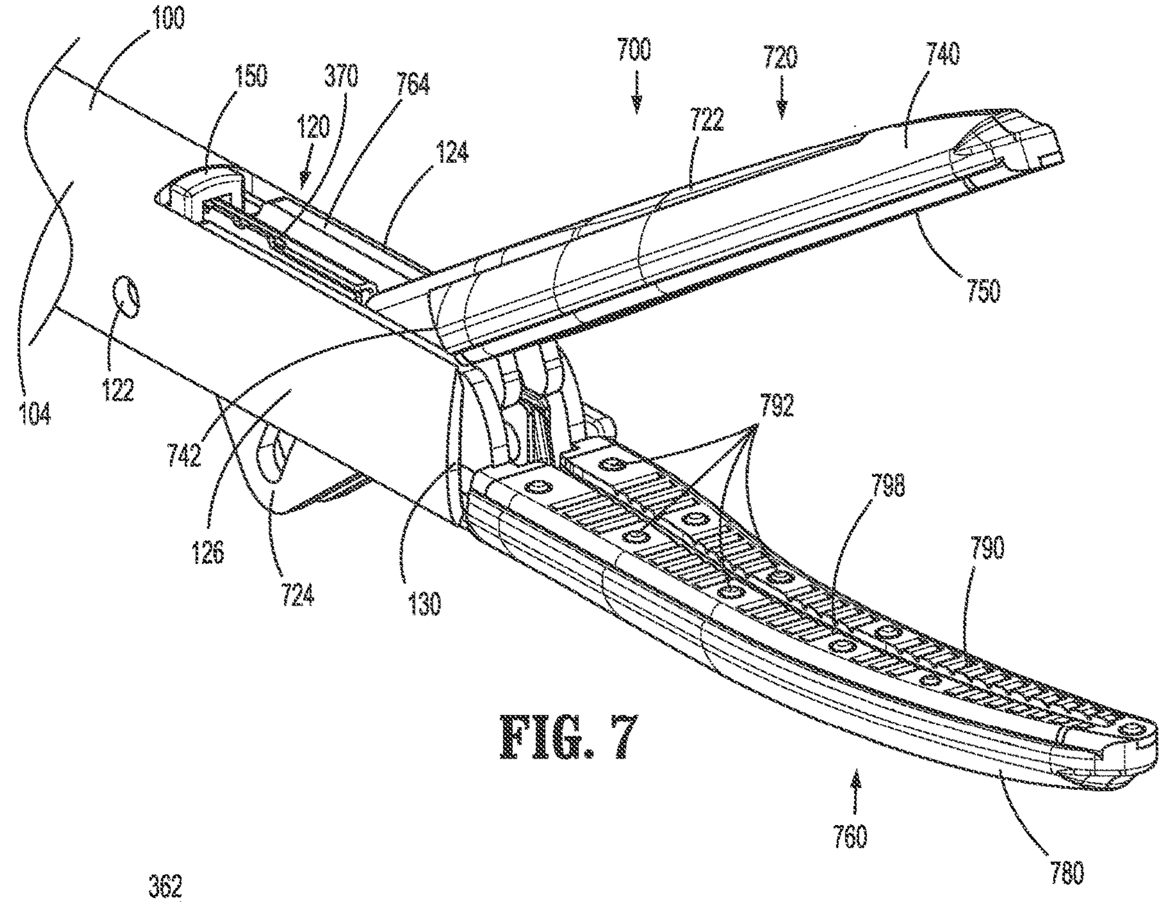
FIG. 7 is a perspective view of the distal portion of FIG. 5 from an opposite side as illustrated in FIG. 5.

Referring again to FIGS. 5-9, the insulative jaw body 740, 780 of each jaw member 720, 760 may be formed from one or more overmolds. For example, a first overmold of insulative material about the structural jaw frame 722, 762 may be provided to define an insulative insert and, subsequent to positioning of the electrically-conductive plate 750, 790 thereon, a second overmold may be provided to secure the electrically-conductive plate 750, 790 to the structural jaw frame 722, 762 and form an outer housing. Alternatively, a single-shot overmold may be utilized, a separate insert may be utilized instead of an overmolded insert, etc. As illustrated in FIG. 6, insulative jaw body 740 of jaw member 720 defines an angled proximal edge 742 on one side thereof that is positioned to oppose and shaped complementary to angled distal edge 130 of flag 126 of clevis 120. In this manner, flag 126 of clevis 120 extends distally beyond at least a portion of angled proximal edge 742, outwardly thereof, thus protecting angled proximal edge 742 and inhibiting angled proximal edge 742 from getting caught and potentially breaking, e.g., upon removal of instrument 10 (FIG. 1) from a trocar (not shown), other manipulation thereof, etc.

Continuing with reference to FIGS. 5-9, electrically-conductive plates 750, 790 are positioned to oppose one another and are electrically-isolated from structural jaw frames 722, 762 via insulative jaw bodies 740, 780, respectively. One or both electrically-conductive plate 750, 790 may include a series of stop members 792 configured to maintain a gap between electrically-conductive plates 750, 790 and inhibit electrical shorting therebetween, e.g., by being formed from an insulative material or by being electrically-isolated from one or both of the electrically-conductive plates 750, 790. Stop members 792 may be the same or different heights and/or the same or different diameters. Further, not all stop members 792 need to contact the opposing electrically-conductive plate 750, 790 to maintain the gap; rather, some stop members 792 may be configured to facilitate gripping tissue. Stop members 792 may be arranged in an asymmetric pattern as illustrated although symmetric configurations are also contemplated.

Each electrically-conductive plate 750, 790 includes a lead wire 754, 794 attached thereto and extending proximally therefrom through shaft 100. More specifically, lead wires 754, 794 are attached, e.g., soldered, to undersides of electrically-conductive plates 750, 790, respectively, and extend proximally through insulative jaw bodies 740, 780, proximally therefrom, and into shaft 100. Lead wires 754, 794 are disposed on opposite sides of end effector assembly 700 and are positioned exteriorly of proximal flag portions 724, 764 of jaw members 720, 760, respectively. Lead wire 754 of jaw member 720, the movable jaw member, extends across, on the interior side thereof, cut-out 128 of flag 124 of clevis 120, thus enabling movement of lead wire 754 as jaw member 720 is pivoted relative to jaw member 760 and clevis 120 without catching of lead wire 754 on clevis 120 or clevis 120 otherwise constraining the movement of lead wire 754 in response to the pivoting of jaw member 720.

Insulative jaw bodies 740, 780 and electrically-conductive plates 750, 790 of jaw members 720, 760, respectively, cooperate to define knife channel portions 758, 798 extending longitudinally therethrough. Knife channel portions 758, 798 define open proximal ends to permit insertion of knife blade 626 therein and closed distal ends that terminate proximally of the distal ends of electrically-conductive plates 750, 790. Knife channel portions 758, 798 define curved configurations that generally conform to the curvature of jaw members 720, 760. In the approximated position of jaw members 720, 760, knife channel portions 758, 798 align with one another to define a full knife channel to facilitate and guide reciprocation of knife blade 626 through jaw members 720, 760 to cut tissue, e.g., treated tissue, grasped therebetween.

As detailed above, clevis 120 defines weld access apertures 122 through the spaced-apart flags 124, 126 thereof that facilitate laser welding of the spaced-apart flags 766, 768 of proximal flag portion 764 of fixed jaw member 760 to flags 124, 126 of clevis 120, respectively, on the respective interior sides of flags 124, 126 of clevis 120. This welding of proximal flag portion 764 of fixed jaw member 760 to flags 124, 126 of clevis 120 captures pivot pin 702 and cam pin 704 between flags 124, 126 of clevis 120, thereby securing pivot pin 702 within aligned pivot apertures 732, 772 of jaw members 720, 760 and securing cam pin 704 within cam slots 730, 770 of members 720, 760. Proximal flag portions 724, 764 of members 720, 760 cooperate with clevis 120 to define a lockbox configuration, adding lateral stability and support to end effector assembly 700.

Jaw member 720 is pivotable relative to jaw member 760 and clevis 120 about pivot pin 702 in response to translation of cam pin 704 through cam slots 730, 770 between a spaced-apart position, wherein electrically-conductive plate 750, 790 are farther apart from one another, and an approximated position, wherein electrically-conductive plates 750, 790 are in closer approximation to one another. More specifically, proximal translation of cam pin 704 through cam slots 730, 770 pivots jaw member 720 towards the approximated position, while distal translation of cam pin 704 through cam slots 730, 770 pivots jaw member 710 towards the spaced-apart position. In the approximated position, jaw members 720, 760 are capable of grasping tissue between electrically-conductive plates 750, 790 thereof. Lead wires 754, 794 are adapted to connect to a source of electrosurgical energy, e.g., an electrosurgical generator (not shown), such that, upon activation, electrically-conductive plates 750, 790 are energized to different potentials to enable the conduction of energy therebetween and through the grasped tissue to treat, e.g., seal, the grasped tissue.

Figure 13:
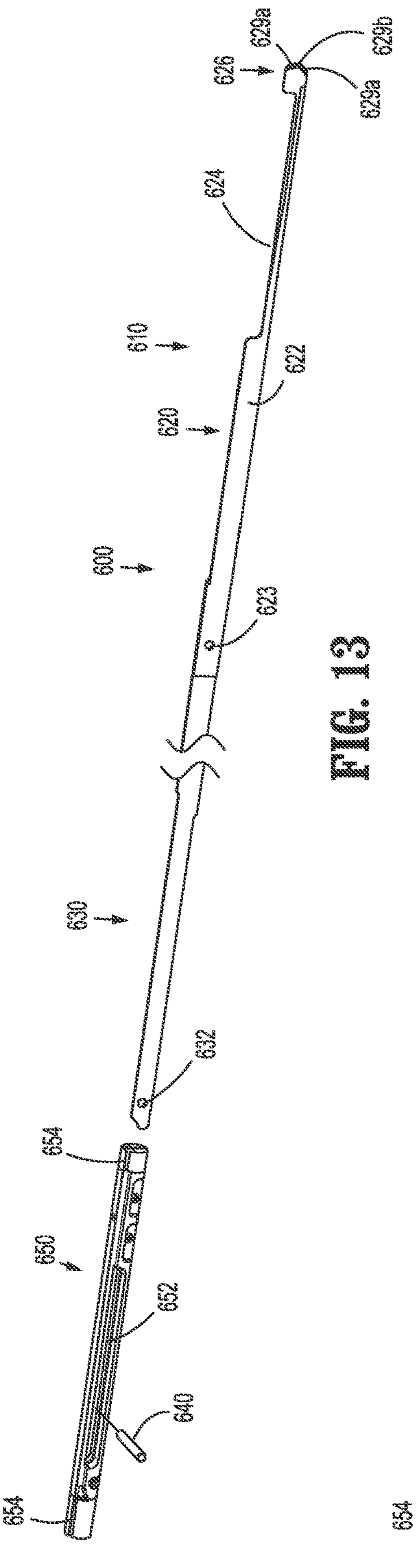
FIG. 13 is an enlarged view of the area of detail indicated as "13" in FIG. 4, providing an exploded, perspective view of a knife assembly of the instrument of FIG. 1.
Figure 14:
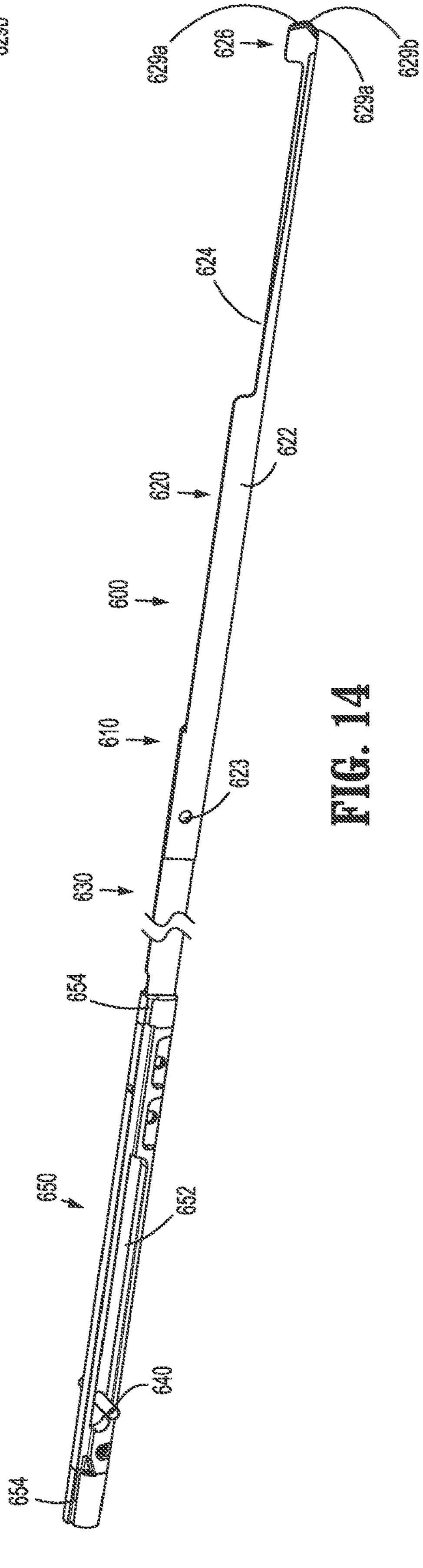
FIG. 14 is a perspective view of the knife assembly of FIG. 13 in an assembled condition.
Figure 15:
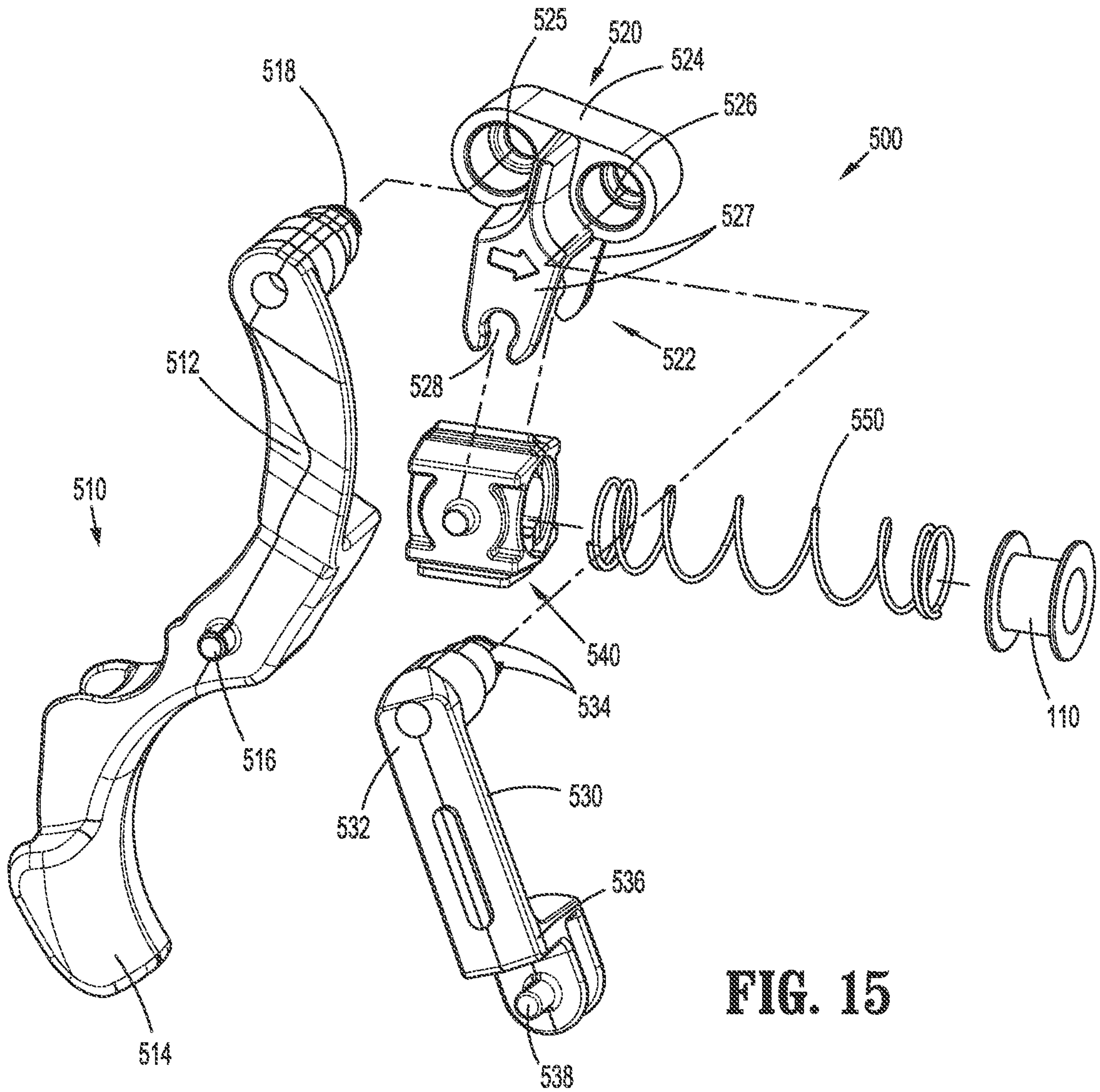
FIG. 15 is an enlarged view of the area of detail indicated as "15" in FIG. 4 providing an exploded, perspective view of a trigger assembly of the instrument of FIG. 1.
Figure 16:
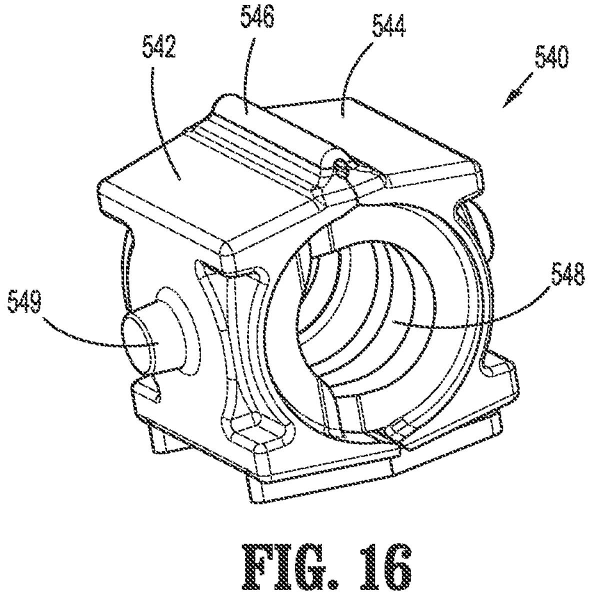
FIGS. 16 and 17 are perspective views of a spindle of the trigger assembly of FIG. 15 in closed and open positions, respectively.
Figure 17:
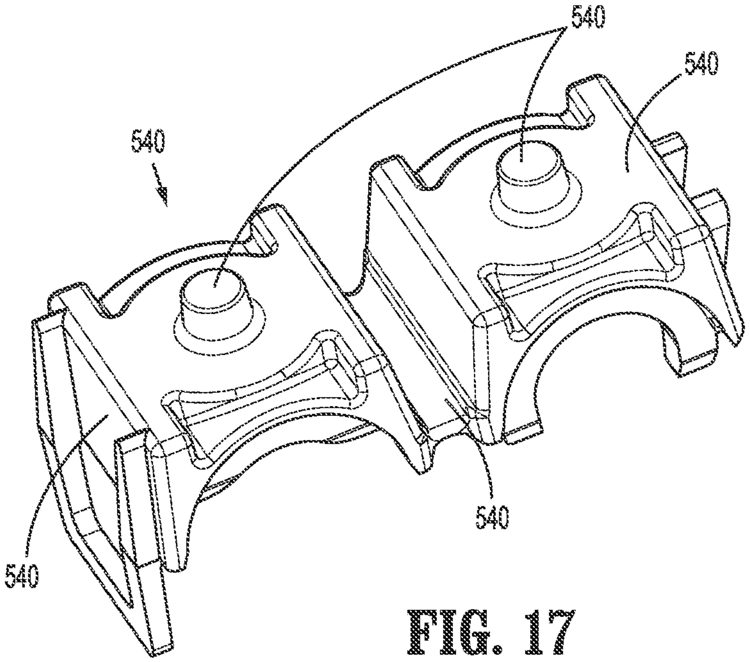
Figure 18:
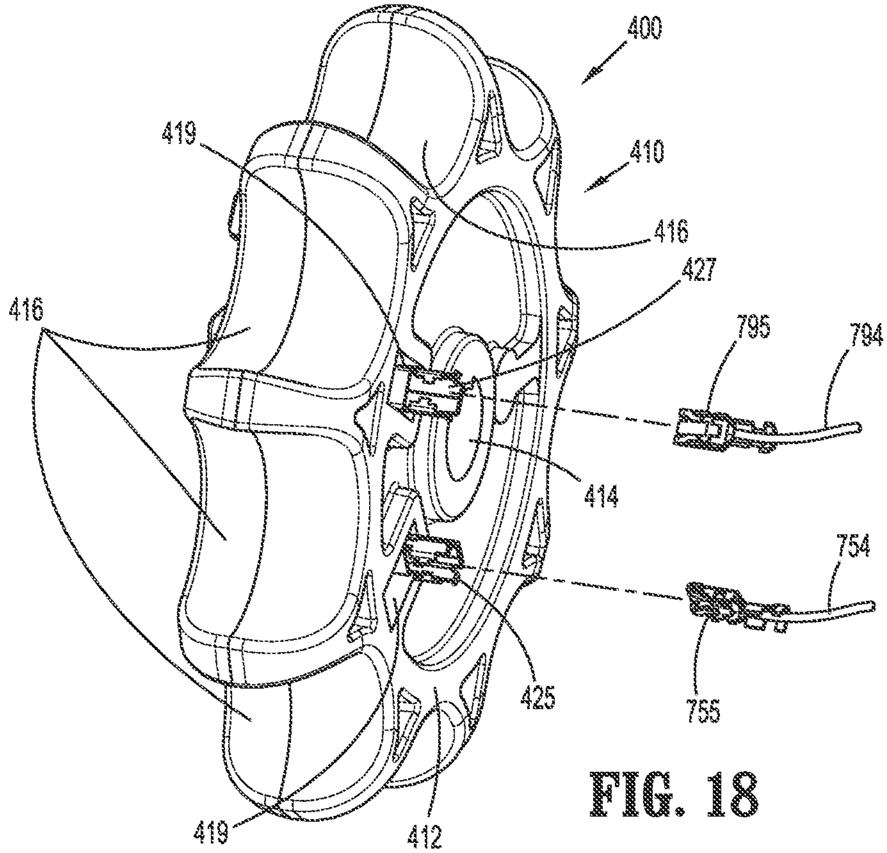
FIG. 18 is an enlarged view of the area of detail indicated as "18" in FIG. 4 providing a perspective view of a rotation assembly of the instrument of FIG. 1.
Figure 19:
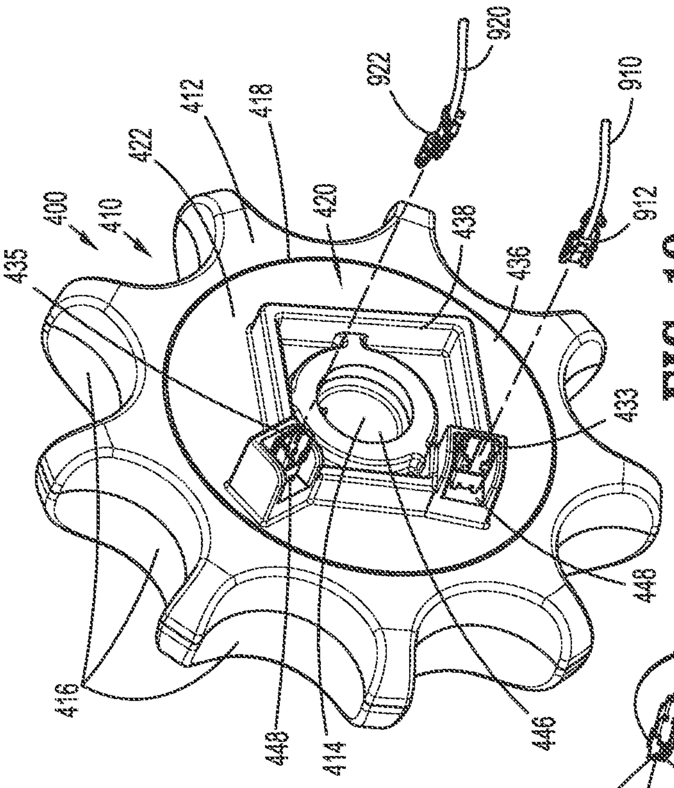
FIG. 19 is another perspective view of the rotation assembly of FIG. 18.
Figure 32:
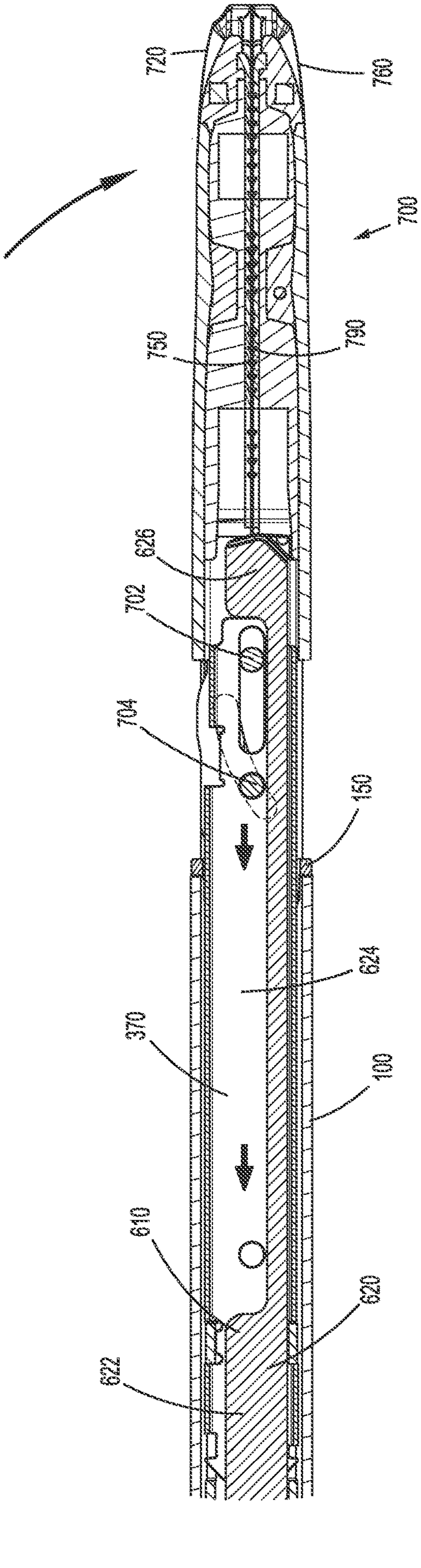
FIG. 32 is an enlarged view of the area of detail indicated as "32" in FIG. 31.

With reference to FIGS. 13 and 14, in conjunction with FIGS. 4 and 7-9, knife assembly 600 includes a knife 610 formed from a distal knife bar 620 and a proximal knife bar 630. Knife assembly 600 further includes a spindle pin 640 and tube plug 650 associated with proximal knife bar 630. Knife 610 is selectively translatable, in response to actuation of trigger assembly 500 (FIG. 4) between a retracted position (see FIG. 32), wherein knife blade 626 of knife 610 is positioned proximally of electrically-conductive plates 750, 790 of jaw members 720, 760, respectively, and an extended position (see FIG. 36), wherein knife blade 626 of knife 610 extends distally through knife channel portions 758, 798 of jaw members 720, 760, respectively, to cut tissue, e.g., treated tissue, grasped therebetween.

Distal knife bar 620 is formed by an etching process (or in any other suitable manner) and includes a body 622 defining a longitudinally-extending cut-out 624 and a knife blade 626 at a distal end thereof, distally of longitudinally-extending cut-out 624. A proximal end portion of body 622 of distal knife bar 620 overlaps a distal end portion of proximal knife bar 630 in side-by-side arrangement to enable securement therebetween, e.g., via laser welding. A laser weld aperture 623 may be defined through body 622 to facilitate such securement. Alternatively or additionally, a weld aperture may be defined through proximal knife bar 630 for similar purposes.

Distal knife bar 620 defines a reduced height as a result of and along the extent of longitudinally-extending cut-out 624. This reduced height portion of distal knife bar 620 enables distal knife bar 620 to extend underneath pivot pin 702 and cam pin 704 (see FIGS. 29 and 32) and defines a suitable length such that the greater-height portions of distal knife bar 620 do not interfere with and are not interfered by pivot pin 702 and cam pin 704 regardless of the relative positioning between pivot pin 702, cam pin 704, and distal knife bar 620.

Knife blade 626 defines an etched distal cutting edge 628 that may define a generally arrow-shaped configuration wherein first and second angled cutting edges 629*a* angle proximally from a distal apex 629*b*. Distal cutting edge 628 may be formed via etching on one side of knife blade 626 or both sides thereof and is sharp to facilitate cutting through tissue upon translation of knife blade 626 to the extended position.

Proximal knife bar 630 is formed by a stamping process (or in any other suitable manner, similar or different from the formation of distal knife bar 620) and, as noted above, defines a distal end portion that overlaps the proximal end portion of body 622 of distal knife bar 620 in side-by-side arrangement to enable securement therebetween, e.g., via laser welding. Proximal knife bar 630 is configured for slidable receipt within tube plug 650 and includes a proximal aperture 632 configured for receipt of spindle pin 640 transversely therethrough. Spring pin 640 extends transversely through and outwardly from either side of a longitudinal slot 652 defined within tube plug 650. Longitudinal slot 652 define a suitable length to accommodate translation of spindle pin 640 relative to tube plug 650 to actuate knife blade 626 between the retracted and extended positions.

Figure 30:
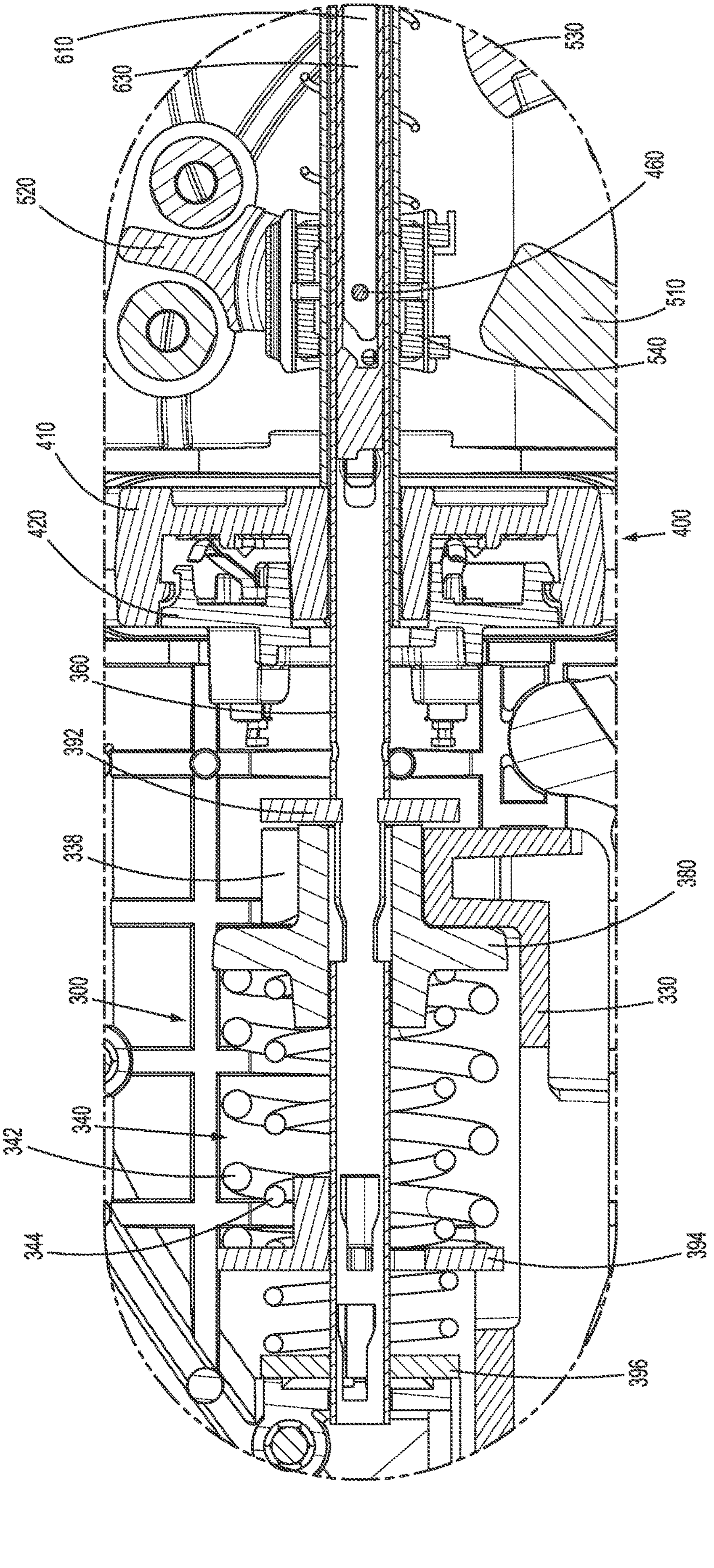
FIG. 30 is an enlarged view of the area of detail indicated as "30" in FIG. 28.
Figure 33:
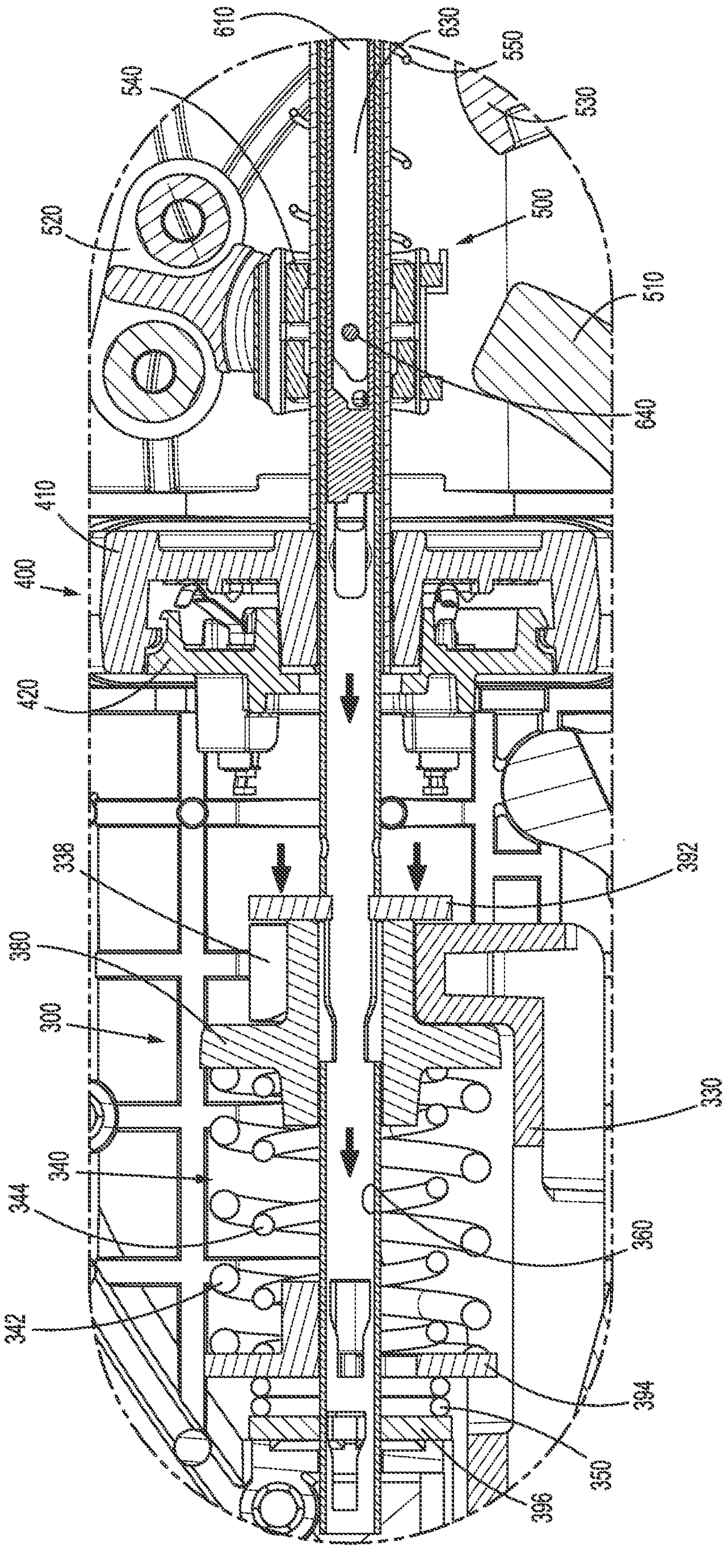
FIG. 33 is an enlarged view of the area of detail indicated as "33" in FIG. 31.

Tube plug 650 is configured for slidable receipt within proximal drive sleeve 360 of drive assembly 300 and servers to maintain the position and orientation of knife 610 therein (see FIGS. 30 and 33). Tube plug 650 further includes one or more wire guide channels 654 on either side thereof to guide lead wires 754, 794 through proximal drive sleeve 360 to end effector assembly 700. Tube plug 650 also serves to substantially inhibit fluid within proximal drive sleeve 360 from passing proximally beyond tube plug 650 and into housing 200.

Figure 31:
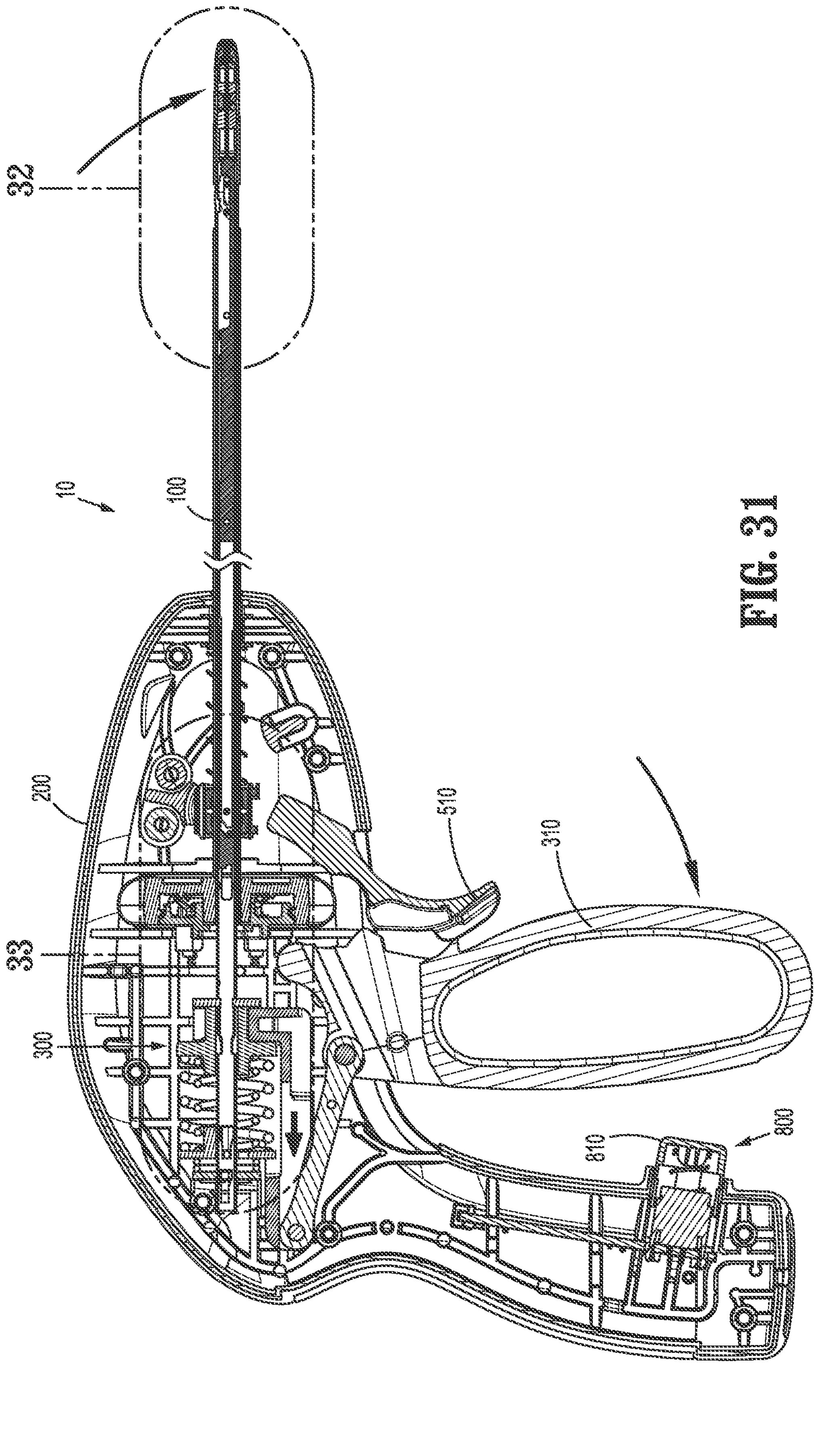
FIG. 31 is a longitudinal, cross-sectional view of the instrument of FIG. 1 illustrating transition of the movable handle from the un-actuated position towards an actuated position.

Referring to FIGS. 2-4, 7-9, 21, and 22, drive assembly 300 is includes a movable handle 310, a linkage 320, a carriage 330, a nested spring assembly 340, a return spring 350, a proximal drive sleeve 360, a distal drive frame 370, a sliding collar 380, first and second fixed (relative to drive sleeve 360) collars 392 and 394, respectively, and a proximal stop collar 396. Movable handle 310 includes a body 312 disposed within housing 200 and having pivot bosses 314 extending transversely outwardly from either side thereof. Body 312 is pivotably coupled to housing 200 within housing 200 via receipt of pivot bosses 314 within movable handle pivot recesses 248 of housing parts 210, 220. Movable handle 310 further includes a grasping portion 318 that depends from body 312 and extends from housing 200 through movable handle and trigger slot 240 to enable manual manipulation by a user. Movable handle 310 is pivotable relative to housing 200 between an un-actuated position (FIG. 28), wherein grasping portion 318 of movable handle 310 is farther spaced-apart from fixed handle portion 290 of housing 200, an actuated position (FIG. 31), wherein grasping portion 318 is more closely approximated relative to fixed handle portion 290 of housing 200, and an activation position (FIG. 34), wherein grasping portion 318 is even further approximated towards fixed handle portion 290 of housing 200 to activate activation button 810 of activation assembly 800. Movable handle 310 also includes first and second spaced-apart knife lockout protrusions 316, 317 protruding distally from body 312 and grasping portion 318, respectively.

Linkage 320 is disposed within housing 200, pivotably coupled to body 312 of movable handle 310 at a distal end portion thereof, and pivotably coupled to carriage 330 at a proximal end portion thereof. In this manner, pivoting of movable handle 310 from the un-actuated position towards the actuated position urges linkage 320 proximally and also pivots linkage 320 from a more-angled orientation to a more-longitudinal orientation.

Carriage 330 is slidably received within body portion 280 of housing 200 and, more specifically, includes bosses 332 extending outwardly from either side thereof that are received within guide tracks 246 of housing 200 to guide translation of carriage 330 through and relative to body portion 280 of housing 200. Carriage 330 includes a body 334 defining a seat 336, and a bifurcated neck 338 extending upwardly from body 334 at a proximal end portion thereof on either side of proximal drive sleeve 360, which extends through carriage 330. First fixed collar 392 is fixed about proximal drive sleeve 360, e.g., via keyed engagement, and is positioned distally of bifurcated neck 338 of carriage 330 to define a distal stop to sliding of carriage 330 about drive sleeve 360. Sliding collar 380 is slidably disposed about proximal drive sleeve 360 and is positioned within seat 336 proximally of bifurcated neck 338. Nested spring assembly 340, including an outer compression spring 342 and an inner compression spring 344 nested within outer compression spring 342, is also seated within seat 336 and positioned proximally of sliding collar 380. Inner and outer compression springs 342, 344 are slidably disposed about proximal drive sleeve 360. Second fixed collar 394 is fixed about proximal drive sleeve 360, e.g., via keyed engagement, and is positioned proximally of nested spring assembly 340. Proximal stop collar 396 is fixed within housing 200 and slidable about a proximal end portion of proximal drive sleeve 360. Proximal stop collar 396 may be slidably engaged within a keyway defined within proximal drive sleeve 360 or may be coupled thereto in any other suitable manner. Return spring 350 may be a conical spring and is disposed about proximal drive sleeve 360 between second fixed collar 394 and proximal stop collar 396.

Proximal drive sleeve 360 defines opposed longitudinally-extending slots 364 defined therethrough to enable spindle pin 640 to extend through and outwardly from either side of proximal drive sleeve 360 while still enabling relative sliding of proximal drive sleeve 360 and spindle pin 640 relative to one another. Spindle pin 640 also extends through opposed longitudinally-extending slots 112 of shaft 100 and outwardly from either side thereof. Slots 112, 364 at least partially overlap regardless of the relative position between proximal drive sleeve 360 and shaft 100 such that spindle pin 640 is not interfered with. Slots 112, 364 also provide a passage for lead wires 754, 794 to extend therethrough, enabling lead wires 754, 794 to extend from rotation assembly 400 (external of shaft 100 and proximal drive sleeve 360) through slots 112, 364 and into proximal drive sleeve 360 (which is disposed within shaft 100). As slots 112, 364 at least partially overlap regardless of the relative position between proximal drive sleeve 360 and shaft 100, lead wires 754, 794 are likewise not interfered with.

Figure 8:
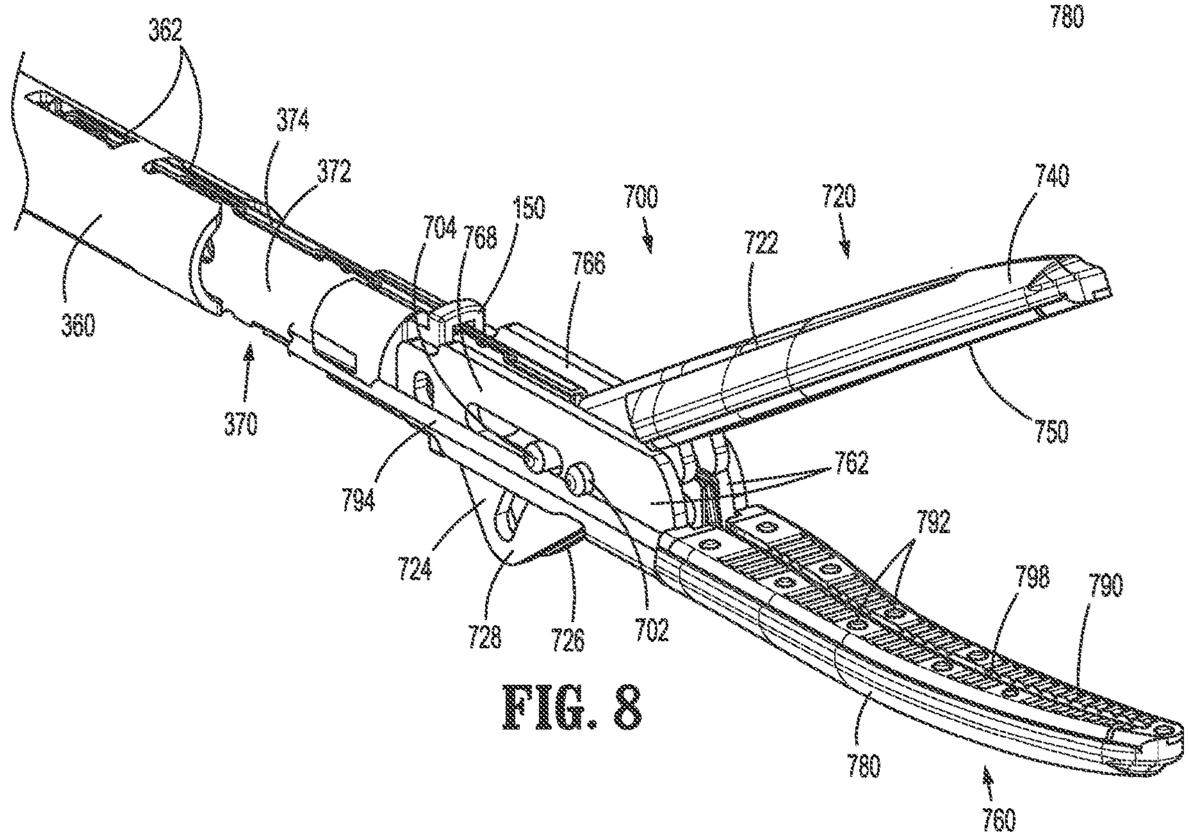
FIG. 8 is a perspective view of the distal portion as illustrated in FIG. 7, with an outer shaft removed to illustrate internal features therein.
Figure 9:
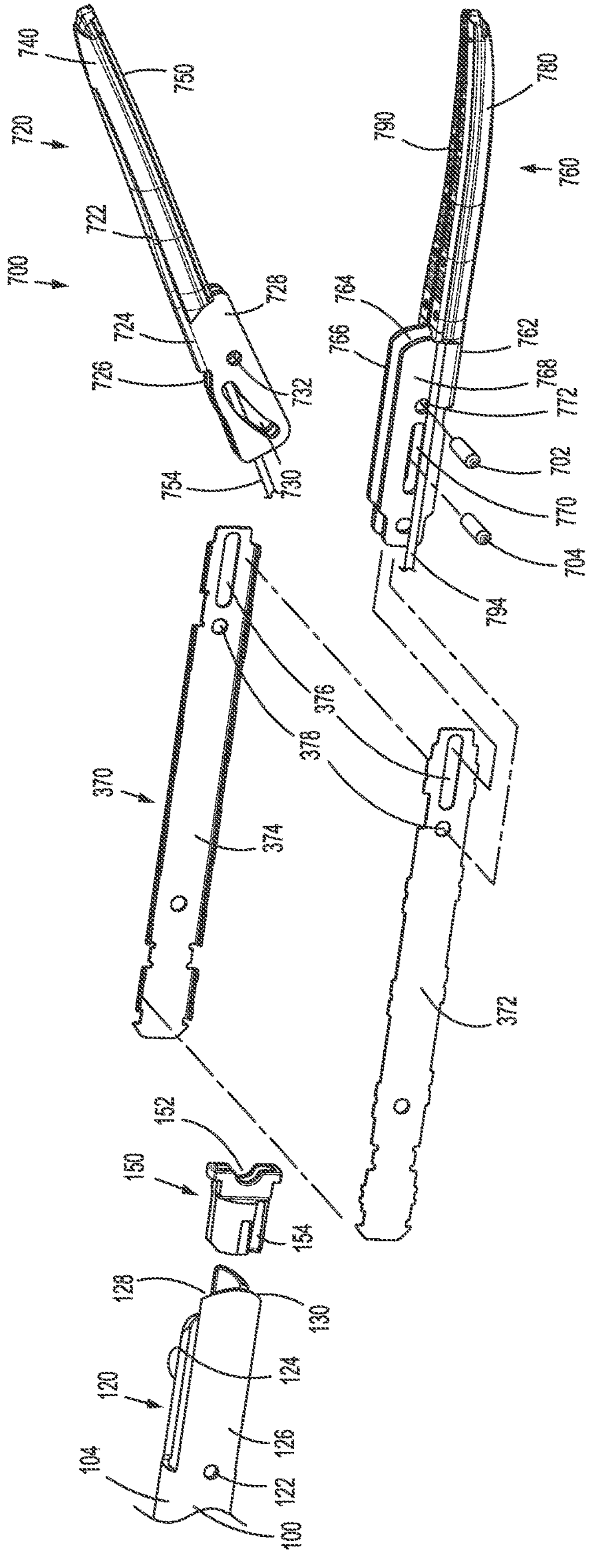
FIG. 9 is an enlarged view of the area of detail indicated as "9" in FIG. 4.

With particular reference to FIGS. 8 and 9, proximal drive sleeve 360 extends distally from housing 200 through shaft 100 to distal drive frame 370. Distal drive frame 370 includes first and second frame plates 372, 374 secured to and extending distally from a distal end portion of proximal drive sleeve 360. First and second frame plates 372, 374 and the distal end portion of proximal drive sleeve 360, more specifically, include complementary engagement features 362 that capture first and second frame plates 372, 374 within the distal end portion of proximal drive sleeve 360. First and second frame plates 372, 374 are vertically oriented and configured to slidably receive and guide distal knife bar 620 of knife 610 therebetween. First and second frame plates 372, 374 further include aligned longitudinal slots 376 and aligned transverse apertures 378 that are configured to receive pivot pin 702 and cam pin 704, respectively. As such, upon translation of proximal drive sleeve 360, distal drive frame 370 is translated to thereby translate cam pin 704 relative to jaw members 720, 760 to pivot jaw member 720 between the spaced-apart and approximated positions.

A distal tube guide 150 is disposed between flags 124, 126 of clevis 120 at the fixed proximal ends thereof and extends proximally into distal end portion 104 of shaft 100. Distal tube guide 150 defines a vertical slot 152 configured to slidably receive and guide translation of distal drive frame 370. Distal tube guide 150 further includes a wire guide channel 154 on either side thereof. Wire guide channels 154 are configured to guide lead wire 754, 794 from jaw members 720, 760 about distal drive frame 370, into distal end portion 104 of shaft 100 and, from there, into proximal drive sleeve 360.

Referring again to FIGS. 2-4, 7-9, 21, and 22, and with additional reference to FIGS. 28-33, as a result of the above-detailed configuration, upon actuation of movable handle 310 from the un-actuated position towards the actuated position (and/or though the actuated position to the activated position), movable handle 310 urges linkage 320 proximally which, in turn, slides carriage 330 proximally. Proximal sliding of carriage 330 urges bifurcated neck 338 into sliding collar 380, thereby urging sliding collar 380 proximally. As sliding collar 380 is urged proximally, sliding collar 380 is urged into nested spring assembly 340. Initially, sliding collar 380 urges springs 342, 344 of nested spring assembly 340 to translate proximally without further compression of springs 342, 344 (springs 342, 344 are pre-compressed during assembly). Springs 342, 344, in turn, urge second fixed collar 394 proximally which thereby pushes proximal drive sleeve 360 proximally and compresses return spring 350 against proximal stop collar 396. The proximal movement of proximal drive sleeve 360 pulls distal drive frame 370 proximally such that cam pin 704 is pulled proximally relative to end effector assembly 700 to thereby pivot jaw member 720 relative to jaw member 760 from the spaced-apart position towards the approximated position.

When a force resisting further approximation of jaw member 720 towards jaw member 760, e.g., a force of tissue resisting compression, is sufficiently great, e.g., large enough to overcome the spring force of springs 342, 344, sliding collar 380 no longer urges springs 342, 344 of nested spring assembly 340 to translate proximally to further approximate jaw member 720 towards jaw member 760. Rather, in this condition, sliding collar 380 is urged into nested spring assembly 340 and compresses springs 342, 344 against second fixed collar 394 while second fixed collar 394 remains substantially stationary within housing 200. Thus, springs 342, 344 compress to absorb further motion of movable handle 310, linkage 320, and carriage 330, allowing proximal drive sleeve 360 and movable jaw member 720 to remain substantially stationary, thus inhibiting application of additional jaw force to tissue grasped between jaw members 720, 760. In this manner, drive assembly 300 and, in particular, springs 342, 344 thereof, control the application of jaw force to tissue grasped between jaw members 720, 760. Instrument 10 (FIG. 1) may be configured to provide a jaw force to tissue (measured at a midpoint along the lengths of electrically-conductive plates 750, 790 of jaw members 720, 760 in the approximated position grasping tissue therebetween) of about 3 $kg/cm^2$ to about 16 $kg/cm^2$.

Springs 342, 344 of nested spring assembly 340 are configured to control jaw force to within a desired range, e.g., 3 $kg/cm^2$ to about 16 $kg/cm^2$, and/or to limit jaw force to or below a threshold value. A single compression spring, based on the design considerations for instrument 10, would be required to have a diameter of about 0.75 inches and a pre-loaded length of about 1.10 inches in order to provide the requisite force(s) for controlling jaw force. In order to provide a more compact design, nested springs 342, 344 are utilized in place of a single compression spring and provide a pre-loaded length of about 0.85 inches and a diameter of about 0.69 inches, thus providing a more compact configuration. Springs 342, 344 may define the same or different at-rest lengths, spring constants, wire diameters, etc. The overall diameters of springs 342, 344 are different so as to enable spring 344 to be nested within spring 342.

In some configurations, a distal surface of sliding collar 380 and a proximally-facing surface of bifurcated neck 338 define cooperating rotational bearing surfaces, e.g., via application of lubricant therebetween, defined surface features (waves, bumps, etc.) on either or both surfaces, etc., to facilitating relative rotation therebetween when movable handle 310 is disposed in the actuated position corresponding to the approximated position of jaw members 720, 760. Alternatively or additionally, a bearing disc (not explicitly shown) may be disposed between sliding collar 380 and bifurcated neck 338 for similar purposes (with or without lubricant and/or defined surface features). In the actuated position of movable handle 310, bifurcated neck 338 is urged distally (directly or indirectly) into sliding collar 380, increasing friction therebetween, thus significantly increasing the difficulty of rotating shaft 100 (since sliding collar 380 is rotationally fixed about shaft 100 while bifurcated neck 338 is not rotatable with shaft 100). The above-noted bearing feature(s) reduce this friction, thereby facilitating rotation of shaft 100 when movable handle 310 is disposed in the actuated position corresponding to the approximated position of jaw members 720, 760.

Referring still to FIGS. 2-4, 7-9, 21, 22, and 28-33, upon release of movable handle 310, return spring 350 facilitates the return of moveable handle 310 towards the un-actuated position and, thus, the return of jaw member 720 towards the spaced-apart position. That is, the bias of return spring 350 towards a more elongated configuration urges second fixed collar 394 distally, thereby urging proximal drive sleeve 360 distally to return jaw member 720 towards the spaced-apart position. The urging of second fixed collar 394 distally also urges nested spring assembly 340 distally to, in turn, urge carriage 330 distally and thereby urge linkage 320 distally such that movable handle 310 is urged towards the un-actuated position.

The above-detailed drive assembly 300 also provides an over-center or near-over-center mechanism with respect to pivot bosses 314 and the pivot points about which linkage 320 is pivotably coupled with movable handle 310 and carriage 330. That is, pivoting of movable handle 310 from the un-actuated position towards the actuated position urges linkage 320 proximally and also pivots linkage 320 from a more-angled orientation to a more-longitudinal orientation, thereby moving the pivot point about which linkage 320 is pivotably coupled with movable handle 310 towards or, in some configuration, into, longitudinal alignment with pivot bosses 314 and the pivot point about which linkage 320 is pivotably coupled with carriage 330. This over-center or near-over-center configuration provides mechanical advantage that reduces the force necessary to urge movable handle 310 to the actuated position.

With reference to FIGS. 2-4, 15-17, and 23, trigger assembly 500 includes a trigger 510, a rocker 520, a linkage 530, a spindle housing 540, and a biasing spring 550. Trigger 510 includes a drive portion 512 disposed within housing 200 and a finger tab 514 that extends through movable handle and trigger slot 240 and from housing 200 to enable manual manipulation thereof. A pair of outwardly-extending pivot bosses 516 extend outwardly from trigger 210 between drive portion 512 and finger tab 514. Pivot bosses 516 are received within first trigger assembly pivot recesses 250 of housing 200 to thereby pivotably couple trigger 210 with housing 200. The free end of drive portion 512 of trigger 510 includes a pair of snap-fit legs 518 extending transversely therefrom.

Rocker 520 defines a "T"-shaped configuration including an upright 522 and a crossbar 524. Cross bar 524 defines first and second snap-fit recesses 525, 526 on either side of upright 522. First snap-fit recess 525 is configured to receive, in snap-fit engagement, snap-fit legs 518 of trigger 510 to pivotably couple drive portion 512 of trigger 510 with rocker 520. Upright 522 defines a bifurcated configuration including first and second spaced-apart bodies 527 extending from crossbar 524 to free ends thereof. Forked connectors 528 are defined at the free ends of first and second spaced-apart bodies 527.

Linkage 530 includes a first end 532 having a pair of snap-fit legs 534 extending transversely therefrom. Snap-fit legs 534 are configured for receipt, in snap-fit engagement, within second snap-fit recess 526 of crossbar 524 to pivotably couple linkage 530 with rocker 520. Linkage 530 further includes a second end 536 defining a pair of pivot bosses 538 extending outwardly therefrom. Pivot bosses 538 are pivotably received within second trigger assembly pivot recesses 252 of housing 200 to pivotably couple second end 536 of linkage 530 with housing 200. The above-detailed configuration of trigger 510, rocker 520, linkage 530, and housing 200 cooperate to define a four-bar mechanical linkage wherein drive portion 512 of trigger 510, crossbar 524 of rocker 520, and linkage 530 serve as the three moving linkages in the four-bar linkage and the portion of housing 200 extending between first and second trigger assembly recesses 250, 252 defines the fixed linkage in the four-bar linkage. The above-detailed pivotable connections between trigger 510 and housing 200, trigger 510 and rocker 520, linkage 530 and rocker 520, and linkage 530 and housing 200 define the four pivot points in the four-bar linkage. A four-bar linkage provides increased mechanical advantage and a compact configuration that and allows for a relatively shorter actuation stroke length of trigger 510 to deploy knife 610 a relatively longer distance.

Continuing with reference to FIGS. 2-4, 15-17, and 23, spindle housing 540 is formed from first and second housing parts 542, 544 monolithically formed as a single component, e.g., via molding, and connected to one another via a living hinge 546. In this manner, housing parts 542, 544 are pivotable about living hinge 546 and relative to one another between an open position, providing access to the interior of spindle housing 540, and a closed position, enclosing the interior of spindle housing 540. Housing parts 542, 544 may include corresponding snap-fit connectors to enable snap-fit connection therebetween to maintain the closed position, although other configurations are also contemplated. In the closed position, spindle housing 540 is configured for slidable and rotatable engagement about shaft 100 and, more specifically, about slots 112, 364 of shaft 100 and proximal drive sleeve 360, respectively. Further, each housing part 542, 544 defines a semi-annular groove on the interior surface thereof such that, in the closed position of spindle housing 540, an annular groove 548 is defined on the interior surface of spindle housing 540. Annular groove 548 is configured to receive, and longitudinally fix, the ends of spindle pin 640 therein such that translation of spindle housing 540 about shaft 100 (and proximal drive sleeve 364) translates spindle pin 640 through slots 112, 364 and relative to shaft 100 and proximal drive sleeve 360, while permitting rotation of spindle pin 640 (and the remainder of knife assembly 600) relative to spindle housing 540. Each housing part 542, 544 also includes a pivot boss 549 extending outwardly therefrom. Pivot bosses 549 are configured to receive, in snap-fit engagement thereabout, forked connectors 528 of spaced-apart bodies 527 of upright 522 of rocker 520 to thereby pivotably couple rocker 520 with spindle housing 540. Biasing spring 550 is disposed about shaft 100 and positioned longitudinally between rocker 520 and proximal collar 110 of shaft 100 to bias spindle housing 540 in a proximal direction.

Figure 28:
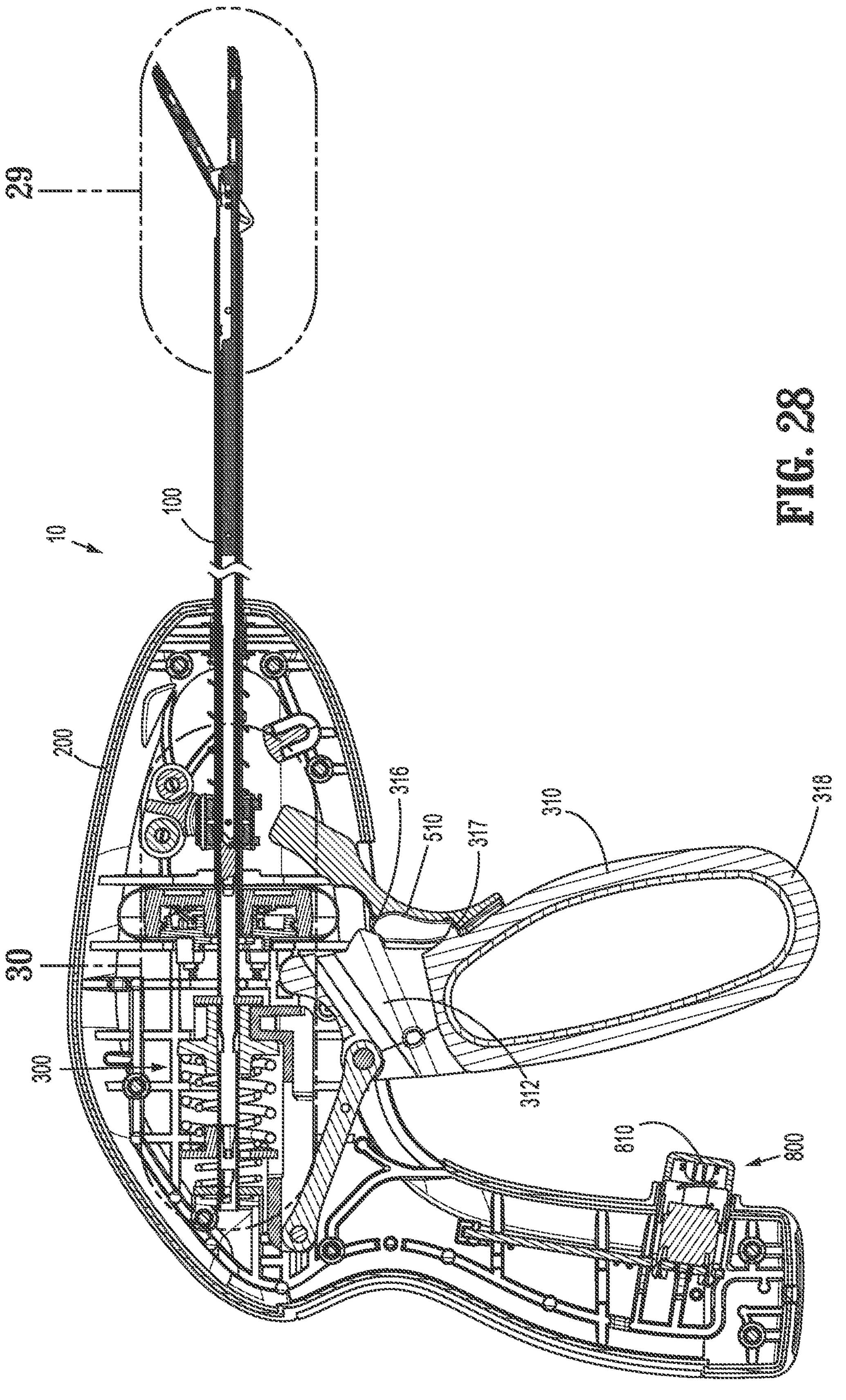
FIG. 28 is a longitudinal, cross-sectional view taken across section line "28-28" of FIG. 1, wherein a movable handle of the drive assembly of the instrument is disposed in an un-actuated position.
Figure 29:
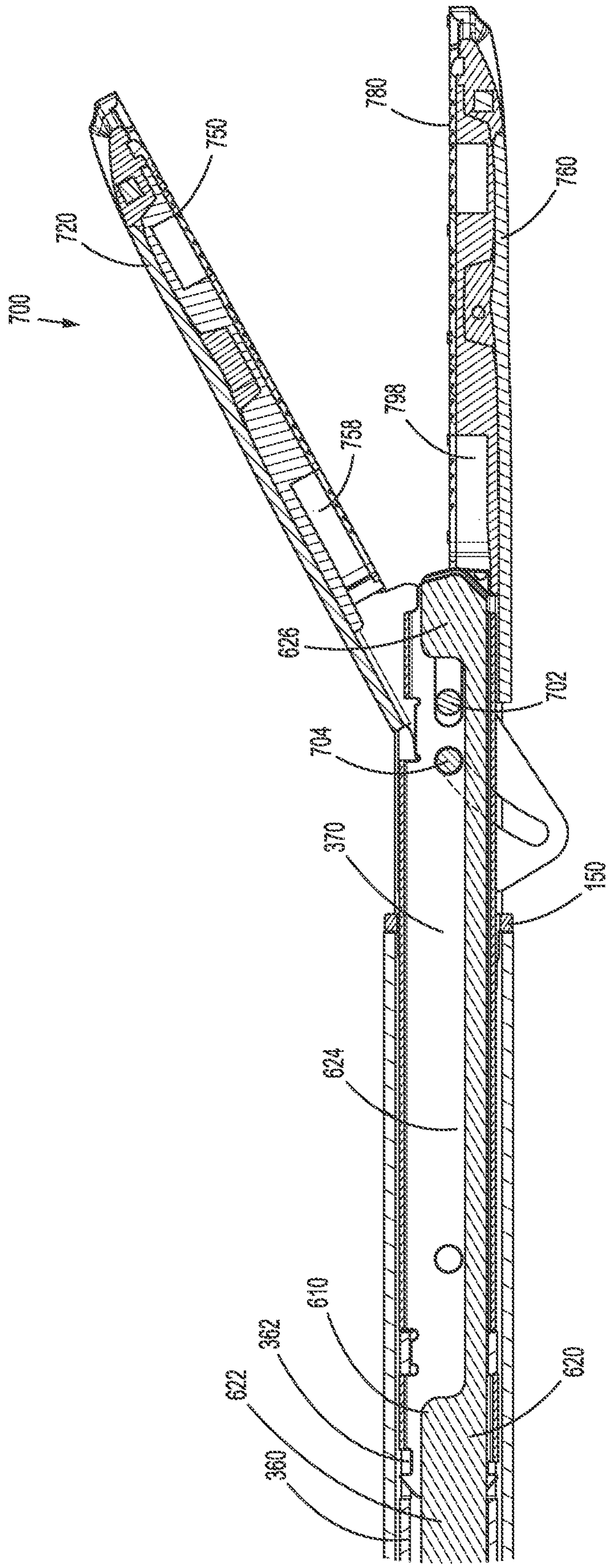
FIG. 29 is an enlarged view of the area of detail indicated as "29" in FIG. 28.

With additional reference to FIGS. 28, 29, and 34-36, in use, and initially with movable handle 310 in the un-actuated position corresponding to the spaced-apart position of j aw members 720, 760, trigger 510 is disposed in an un-actuated position corresponding to the retracted position of knife 610 (see FIGS. 28 and 29). In this position, knife lockout protrusions 316, 317 of movable handle 310 are positioned adjacent to and/or in contact with trigger 510 at spaced-apart positions along the height of trigger 510. Knife lockout protrusions 316, 317 serve to inhibit actuation of trigger 510 when movable handle 310 is disposed in the un-actuated position and, thus, when jaw members 720, 760 are disposed in the spaced-apart position. As an alternative or in addition to both protrusions 316, 317 serving a lockout features, one of the protrusion, e.g., protrusion 317 may facilitate kick-back, that is, return of trigger 510 to the un-actuated position thereof upon return of movable handle 310 towards the un-actuated position thereof.

With movable handle 310 in the actuated position (FIG. 31) (or the activated position (FIG. 34)) and, thus, jaw members 720, 760 disposed in the approximated position (FIG. 32), trigger 510 is permitted to be actuated. In order to actuate trigger 510, with reference to FIGS. 34-36, finger tab 514 of trigger 510 is pivoted proximally towards movable handle 310. Proximal pivoting of finger tab 514 pivots body 512 of trigger 510 distally since body 512 and finger tab 514 are on opposite sides of the pivot connecting trigger 510 with housing 200.

Figure 36:
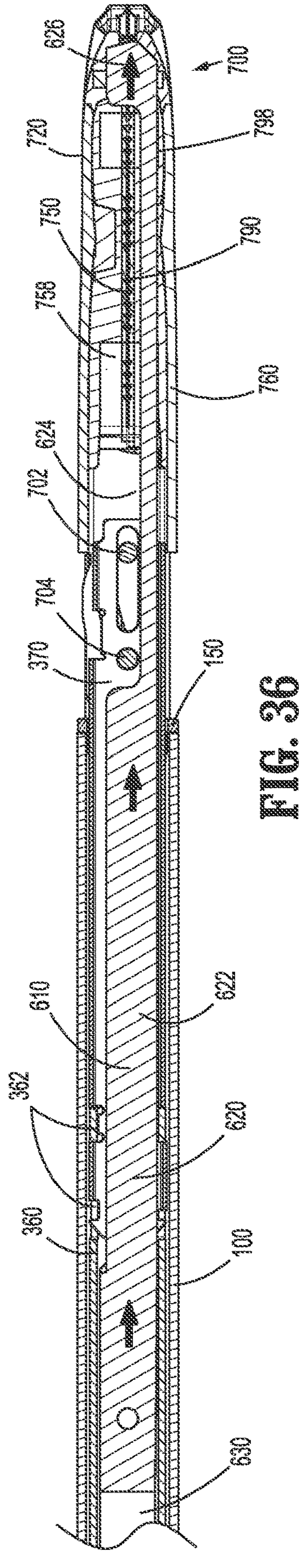
FIG. 36 is a longitudinal, cross-sectional view of a distal portion of the instrument of FIG. 1 illustrating deployment of the knife assembly.
Figure 37:
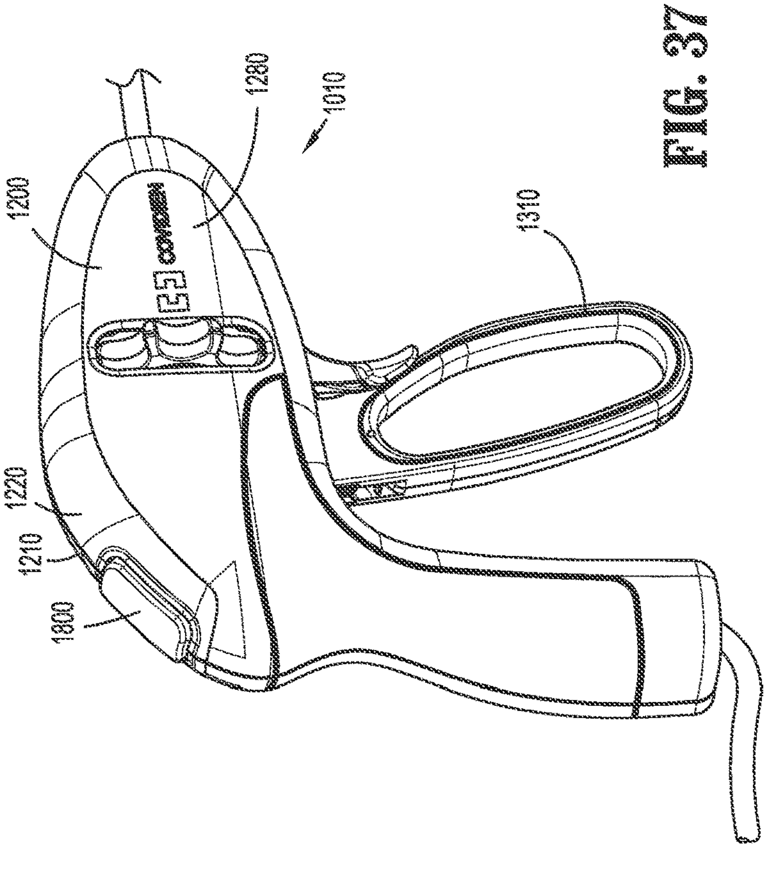
FIG. 37 is a rear perspective view of a proximal portion of another energy-based surgical instrument provided in accordance with the present disclosure.
Figure 38:
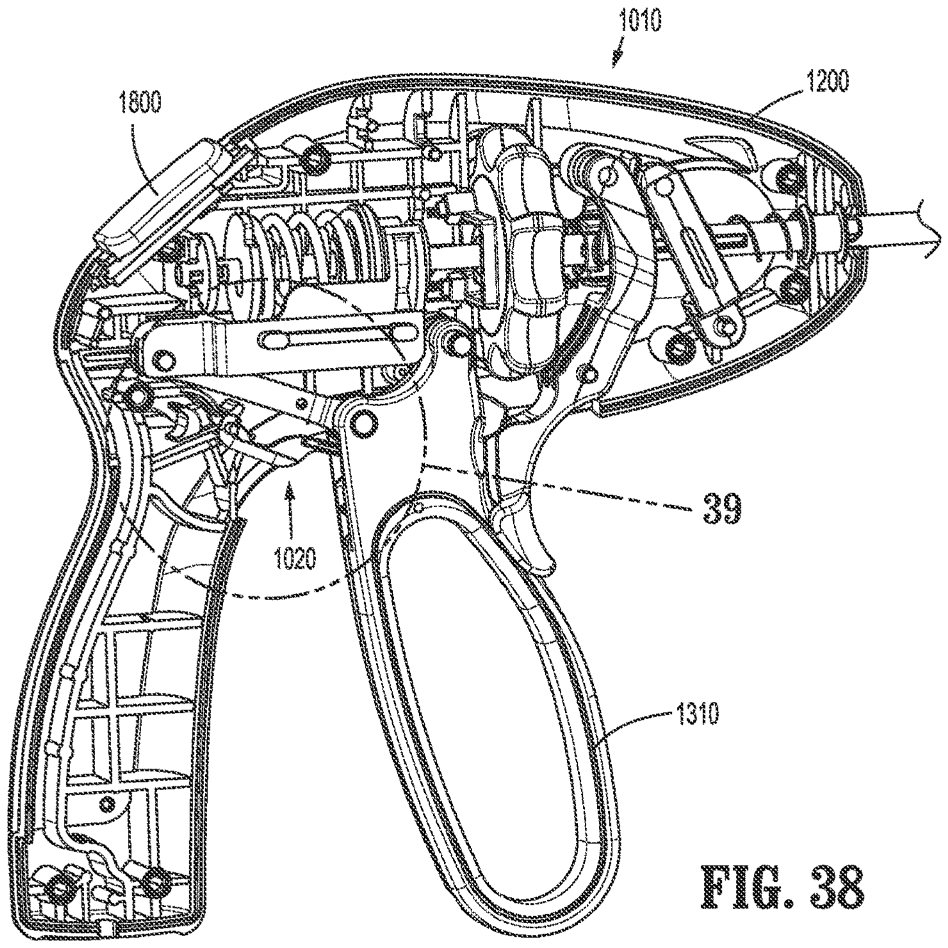
FIG. 38 is a perspective view of the proximal portion of the instrument of FIG. 37 with a portion of the housing removed to illustrate internal features therein.
Figure 39:
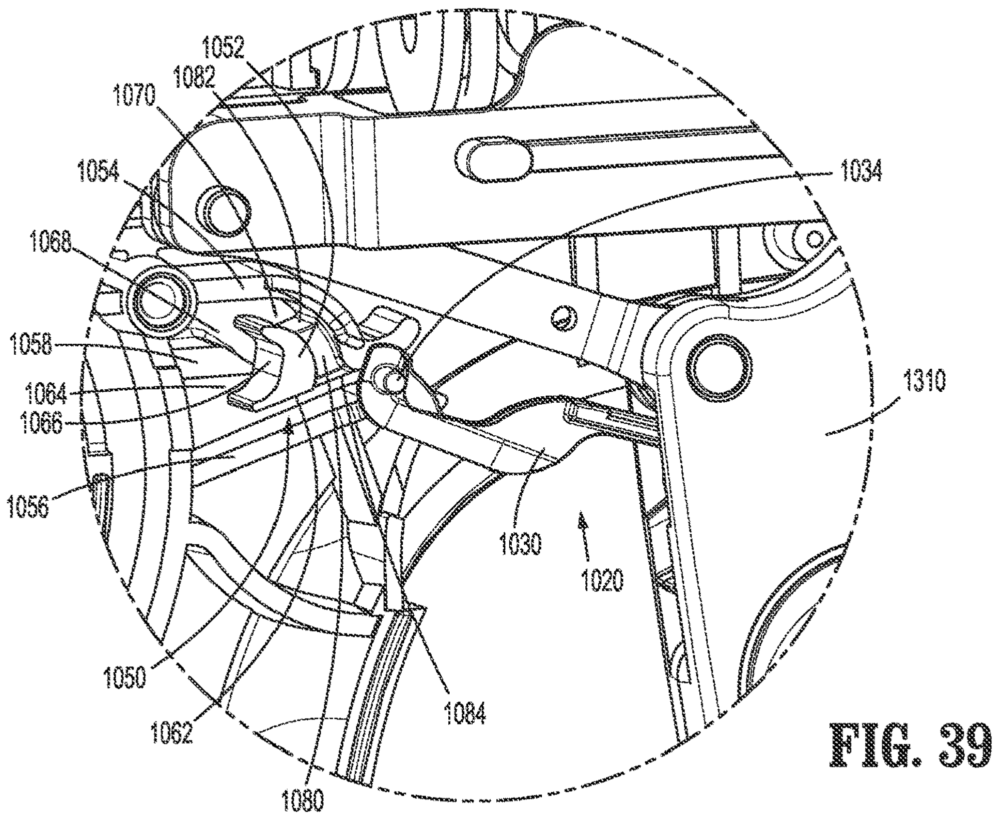
FIG. 39 is an enlarged perspective view of the area of detail indicated as "39" in FIG. 38 illustrating a latch mechanism.
Figure 40:
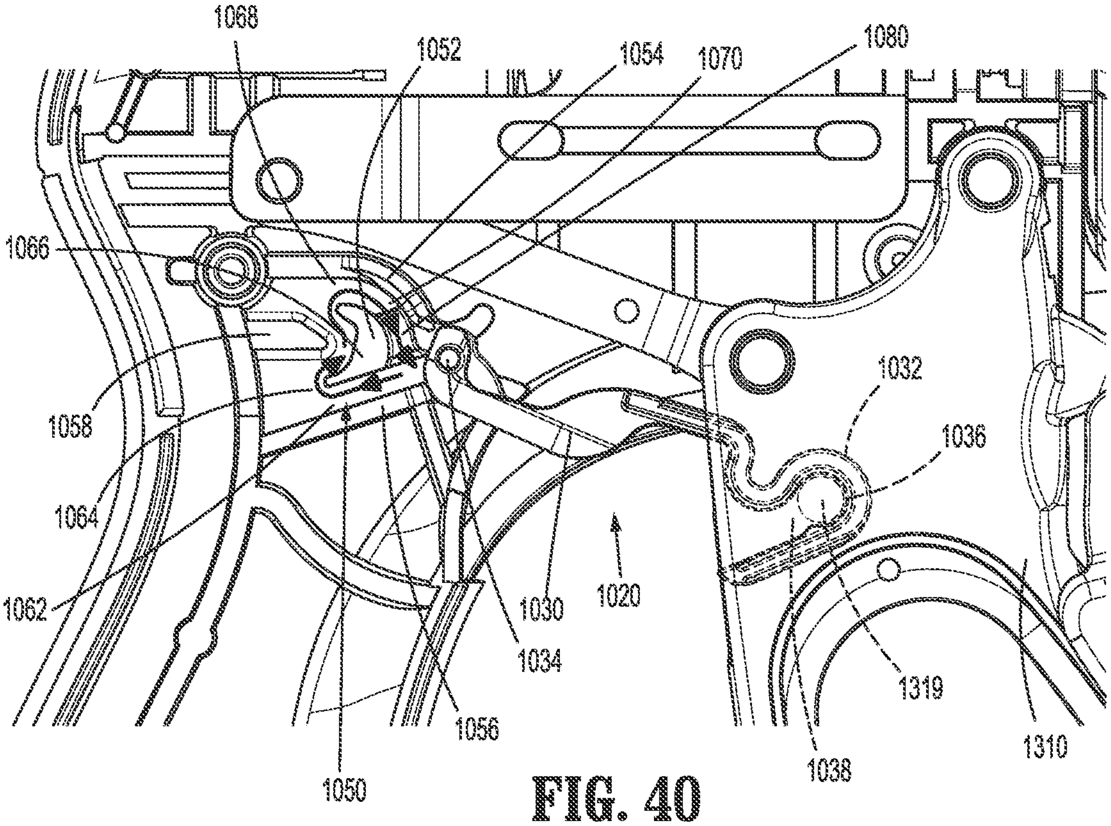
FIG. 40 is an enlarged, side view of the latch mechanism of FIG. 39 in an unlatched condition.
Figure 41:
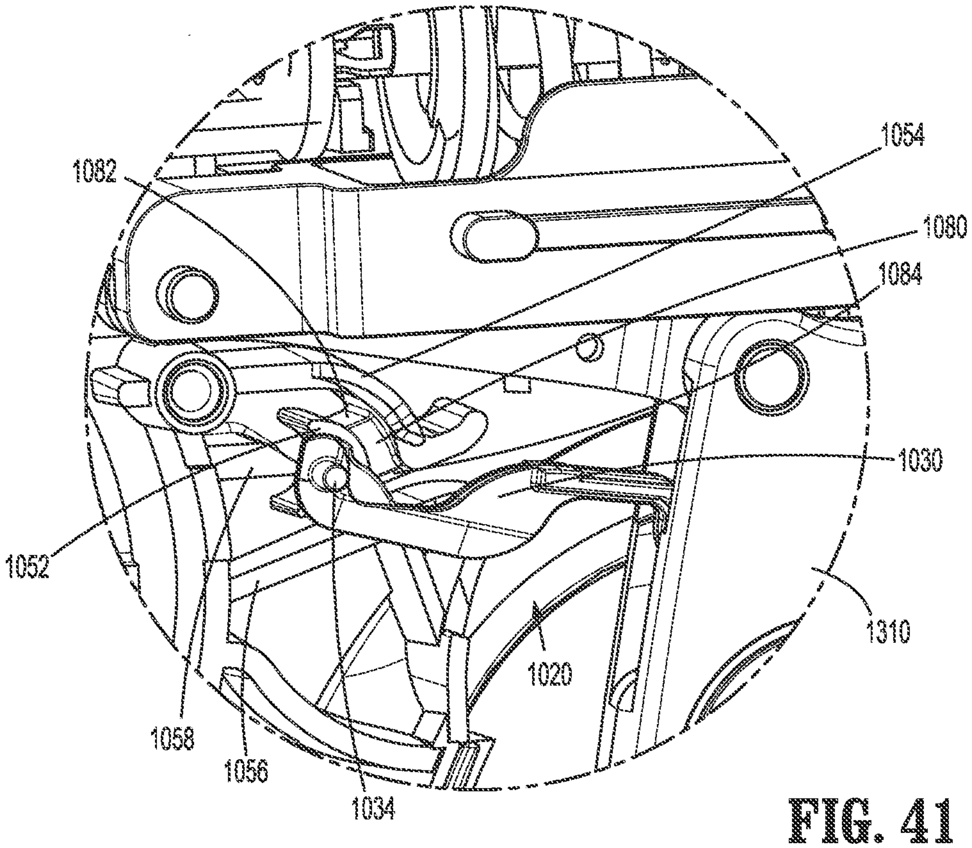
FIG. 41 is an enlarged perspective view of the latch mechanism of FIG. 38 disposed in a latched condition.

Distal pivoting of body 512 of trigger 510 urges crossbar 524 of rocker 520 distally. In order to permit this distal movement of crossbar 524 of rocker 520, linkage 530 is pivoted distally about second end 536 thereof. The distal movement of crossbar 524 of rocker 520 pulls upright 522 of rocker 520 distally and pivots upright 522 relative to spindle housing 540. The distal pulling of upright 522 pulls spindle housing 540 distally along shaft 100 such that spindle pin 640 is translated distally through slots 112, 364 to thereby advance knife 610 distally from the retracted position to the extended position wherein, as shown in FIG. 36, knife blade 626 extends through knife channel portions 758, 798 of jaw members 720, 760 and between electrically-conductive plates 750, 790 of jaw members 720, 760 to cut tissue grasped therebetween. As noted above, tube plug 650, distal drive frame 370, and distal tube guide 150 guide translation of knife 610 between the retracted and extended positions.

The distal translation of spindle housing 540 along shaft 100 to deploy knife 610 compresses spring 550 such that, upon release of trigger 510, the return force of spring 550 urges spindle housing 540 to return proximally, thereby urging rocker 520 to return proximally, linkage 530 to pivot proximally about second end 536 thereof, and urging finger tab 514 of trigger 510 distally back to the un-actuated position thereof.

Turning to FIGS. 2-4, 18-20, 24, 25, 30, and 33, rotation assembly 400 includes a rotation wheel 410 and a continuous rotation assembly 420. Rotation wheel 410 includes a body 412 and a keyed central aperture 414 extending through body 412. Keyed central aperture 414 is configured to receive shaft 100 therethrough and engage proximal cut-out 114 of shaft 110 to thereby fixedly mount rotation wheel 410 about shaft 100. Rotation wheel 410 also includes a plurality of flutes 416 arranged annularly about an annular periphery thereof. Rotation wheel 410 protrudes outwardly through rotation wheel windows 242 defined within housing 200, such that flutes 416 may be manually manipulated by a user to rotate rotation wheel 410 relative to housing 200 from either side of housing 200. Rotation wheel 410 is rotatable continuously in either direction without limitation, e.g., infinitely in either direction. Rotation of rotation wheel 410 rotates shaft 100 relative to housing 200 and, via the interconnections therebetween, also effects rotation of distal tube guide 150, proximal drive sleeve 360, distal drive frame 370, end effector assembly 700, and knife assembly 600 relative to housing 200 in conjunction with the rotation of shaft 100 and rotation wheel 410. In this manner, end effector assembly 700 may be positioned in a desired orientation to facilitate grasping, treating, and/or dividing tissue.

Rotation wheel 410 further defines a proximally-facing recess 418 (see FIGS. 30 and 33) and a pair of pass-through connector slots 419. Pass-through connector slots 419 are configured to receive lead connectors 755, 795 secured at the proximal ends of lead wires 754, 794, respectively, and electrically coupled thereto. Lead wires 754, 794 extend from lead connectors 755, 795, into shaft 100 and proximal drive sleeve 360, distally through proximal drive sleeve 360, about distal drive frame 370, and to jaw members 720, 760 for electrically coupling with electrically-conductive plates 750, 790, respectively, as detailed above. The entireties of lead wires 754, 794 are rotatable in conjunction with the rotation of rotation wheel 410.

Continuous rotation assembly 420 includes a body 422, an inner contact ring 424 including an electrical connector 425 extending therefrom, an outer contact ring 426 including an electrical connector 427 extending therefrom, and first and second spring contacts 432, 434 each including a respective electrical connector 433, 435 extending therefrom. Body 422 is configured for rotatable engagement with rotation wheel 410, e.g., enabling rotation of rotation wheel 410 about body 422 and relative to housing 200, and includes a disc 436 and a frame 438 monolithically formed as a single piece, although other configurations are also contemplated. Disc 436 includes an outer rim 440 and a distally-facing surface 442 recessed relative to outer rim 440. Outer rim 440 of disc 436 is configured for rotatable receipt within proximally-facing recess 418 of rotation wheel 410, e.g., in snap-fit rotation engagement, such that a cavity is defined between distally-facing surface 442 of disc 436 and the recessed surface of proximally-facing recess 418 of rotation wheel 410. Frame 438 is configured to be fixedly captured within housing 200 (See FIG. 25) to thereby fix body 422 within and relative to housing 200. Thus, rotation wheel 410 is rotatable relative to body 422 and housing 200. Body 422 further defines a central aperture 446 configured to rotatably receive shaft 100, and a pair of pass-through connector slots 448. Thus, rotation wheel 410 is rotatable relative to body 422 and housing 200.

Inner and outer contact rings 424, 426 are disposed within the cavity defined between disc 436 and rotation wheel 410 and, more specifically, are fixed relative on and relative to the recessed surface of proximally-facing recess 418 of rotation wheel 410 with electrical connectors 425, 427, respectively, thereof extending into pass-through connector slots 419 to engage and electrically couple with lead connectors 755, 795 of lead wires 754, 794, respectively. Connectors 425, 427 and connectors 755, 795 may be male-female slide connectors configured to slide and lock into engagement and electrical coupling with one another, without the need for tools, soldering, etc. The connection between connectors 425, 427 and connectors 755, 795, respectively, electrically couples lead wires 754, 795 with inner and outer contact rings 424, 426, respectively.

First and second spring contacts 432, 434 are fixedly secured to body 422 and, thus, housing 200, at least via receipt of electrical connectors 433, 435 of spring contacts 432, 434, respectively, within pass-through connector slots 448. Electrical connectors 433, 435 are configured to slide and lock into engagement and electrical coupling with corresponding lead connectors 912, 922 of lead wires 910, 920, e.g., as male-female connectors detailed above. Lead wires 910, 920 are routed through housing 200 to activation assembly 800, which, in turn, is in electrical communication with wires associated with cable 900 to connect to the energy source, e.g., an electrosurgical generator (not shown), via plug 940 of cable 900 (see FIG. 1). The portions of lead wires 910, 920 extending within housing 200 are entirely stationary regardless of rotation of rotation wheel 410.

First and second spring contacts 432, 434 are biased into contact with inner and outer contact rings 424, 426, respectively. More specifically, first and second spring contacts 432, 434 maintain contact with inner and outer contact rings 424, 426, respectively, regardless of the rotational orientation of rotation wheel 410 relative to body 422, thus maintaining electrical connection and permitting continuous, e.g., infinite, rotation of rotation wheel 410 in either direction relative to body 422 and housing 200. The electrical connection between first and second spring contacts 432, 434 and inner and outer contact rings 424, 426, respectively, electrically connects lead wires 910, 920 with lead wires 754, 794, thus enabling the conduction of energy, e.g., electrosurgical energy, from the generator to electrically-conductive plates 750, 790 of jaw members 720, 760, respectively, for treating tissue grasped therebetween (see FIGS. 7-9).

Figure 20:
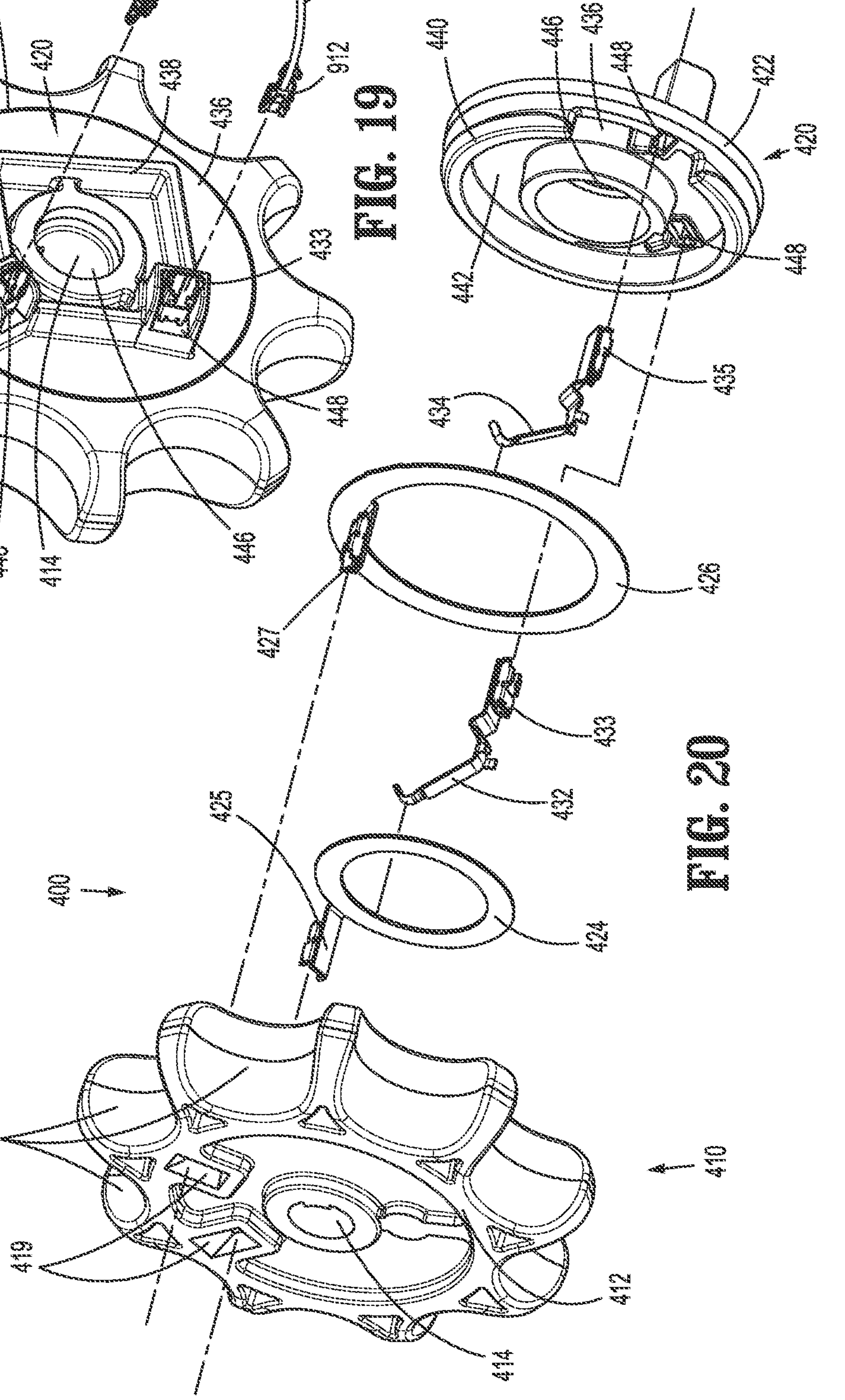
FIG. 20 is an exploded, perspective view of the rotation assembly of FIG. 18.
Figure 20A:
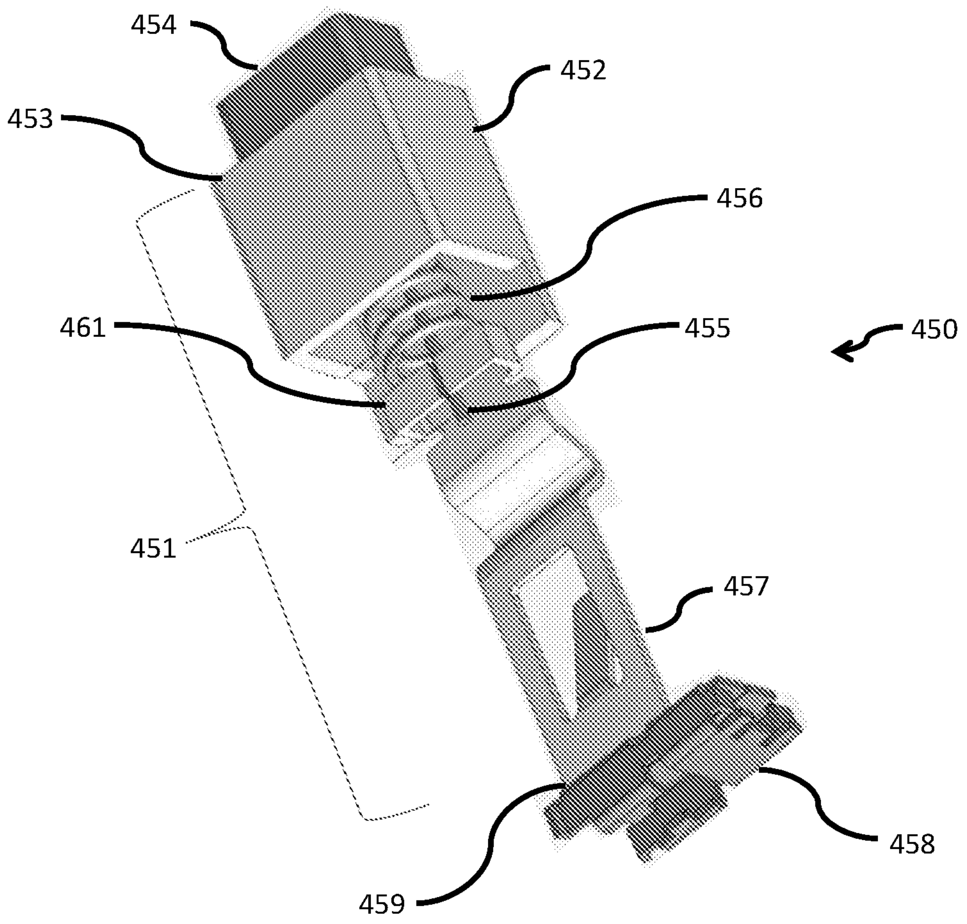
FIG. 20A is a perspective view of another configuration of a spring contact configured for use with the rotation assembly of FIG. 18.
Figure 22:
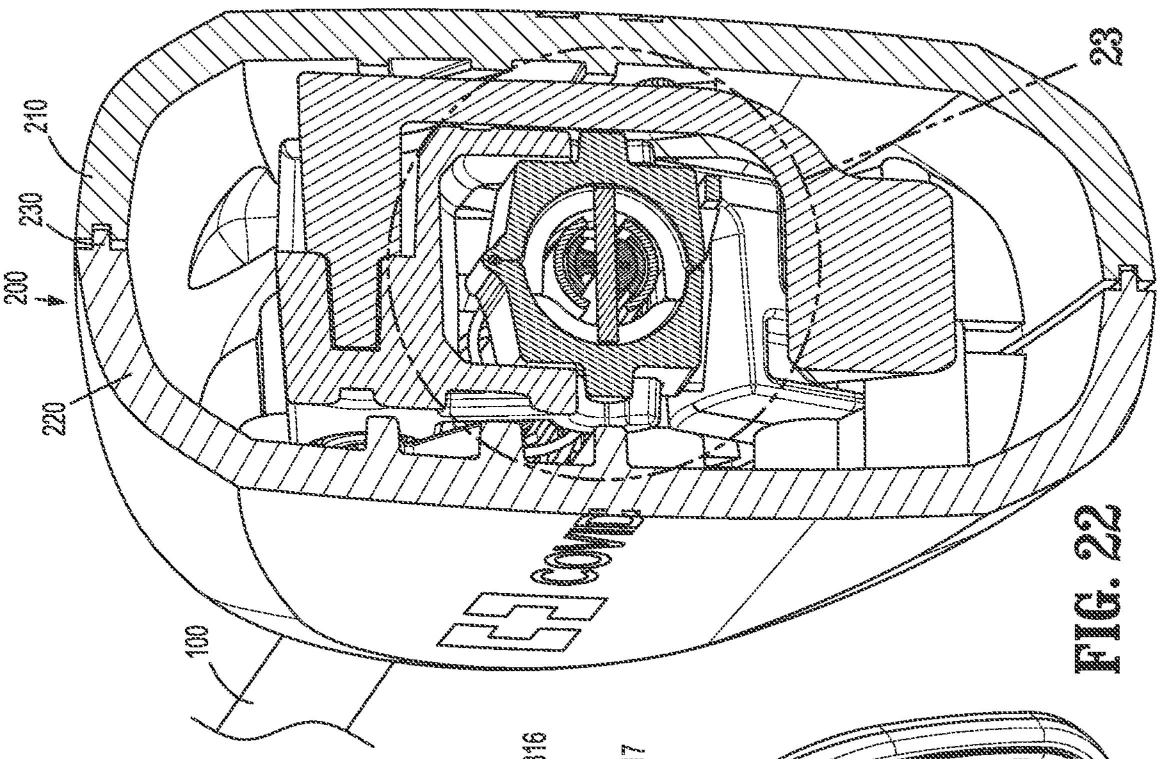
FIG. 22 is a transverse, cross-sectional view taken across section line "22-22" of FIG. 3.
Figure 21:
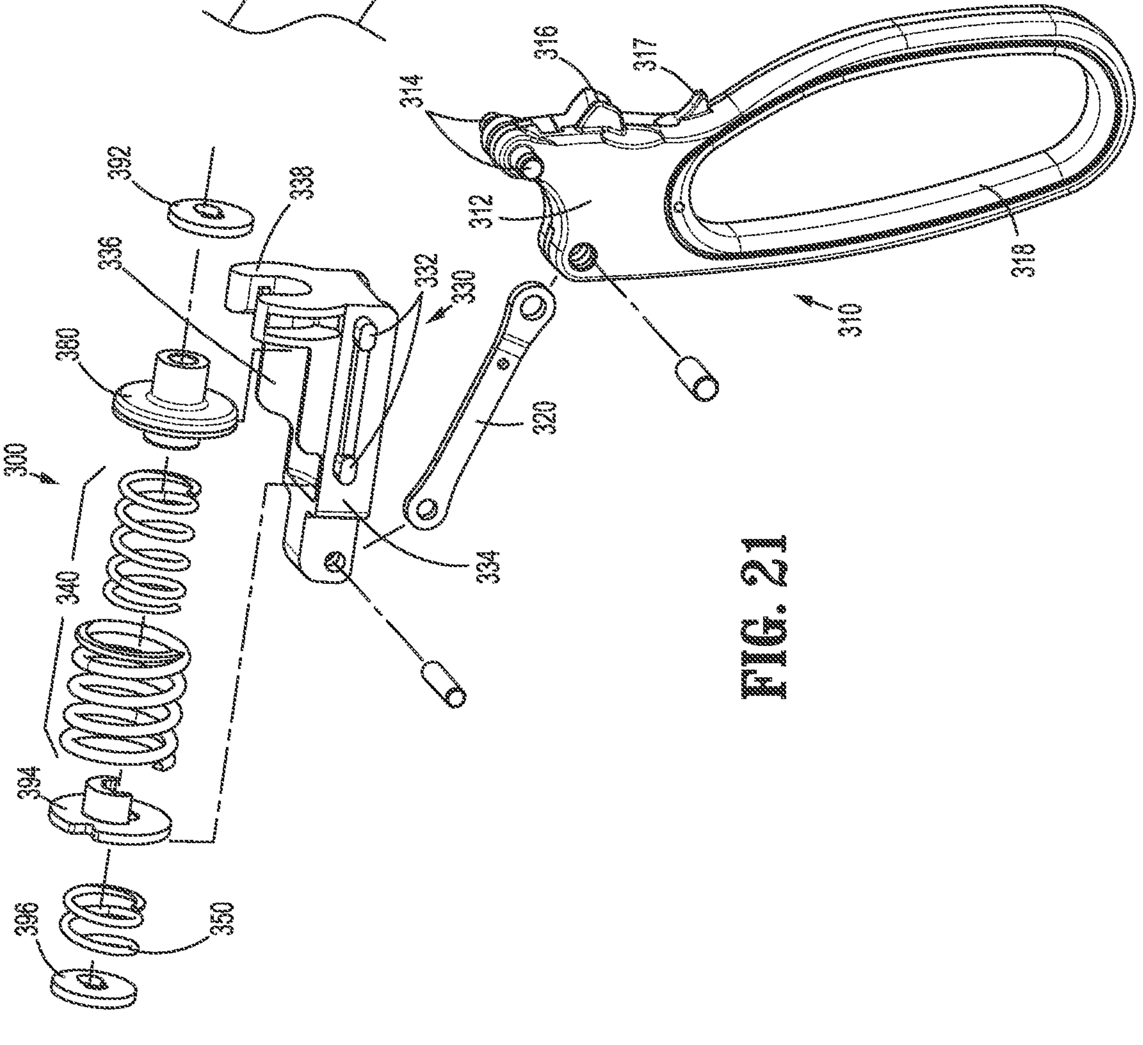
FIG. 21 is an exploded, perspective view of a drive assembly of the instrument of FIG. 1.
Figure 24:
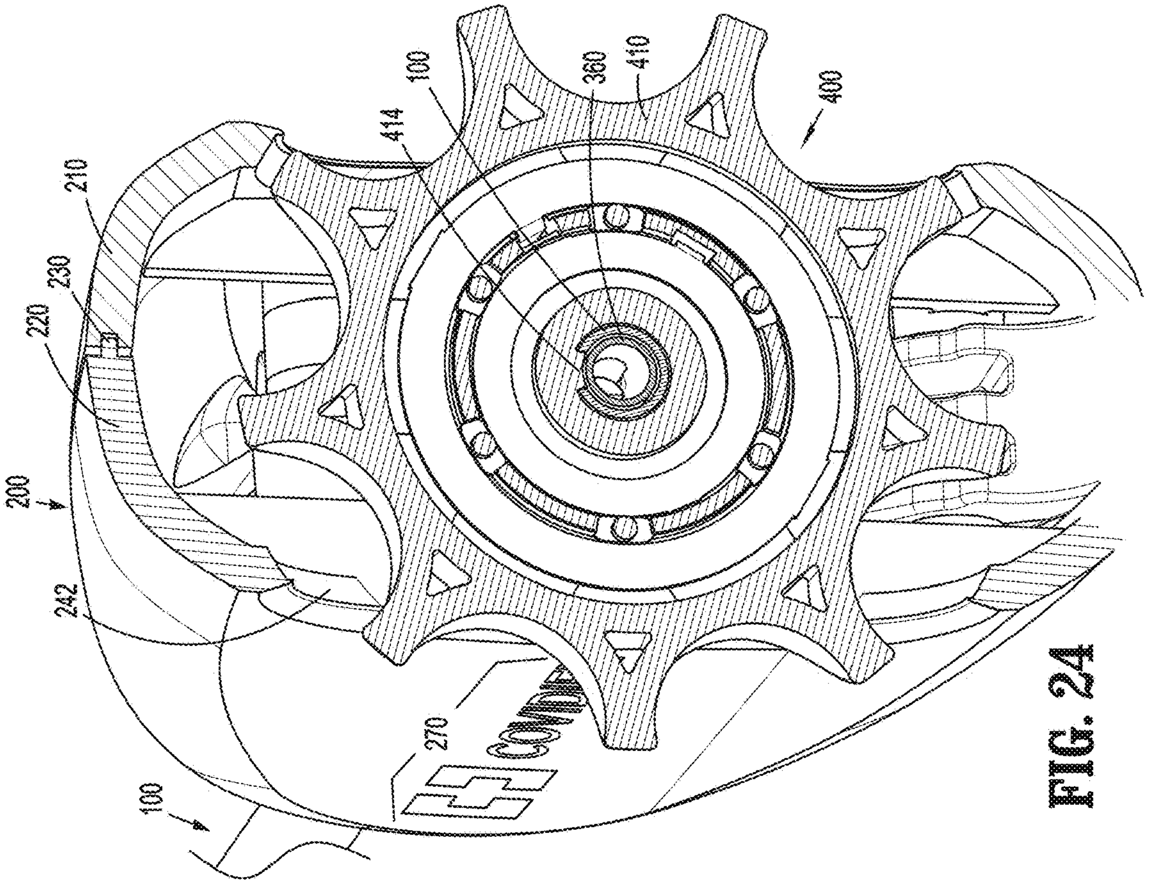
FIG. 24 is a transverse, cross-sectional view taken across section line "24-24" of FIG. 3.
Figure 23:
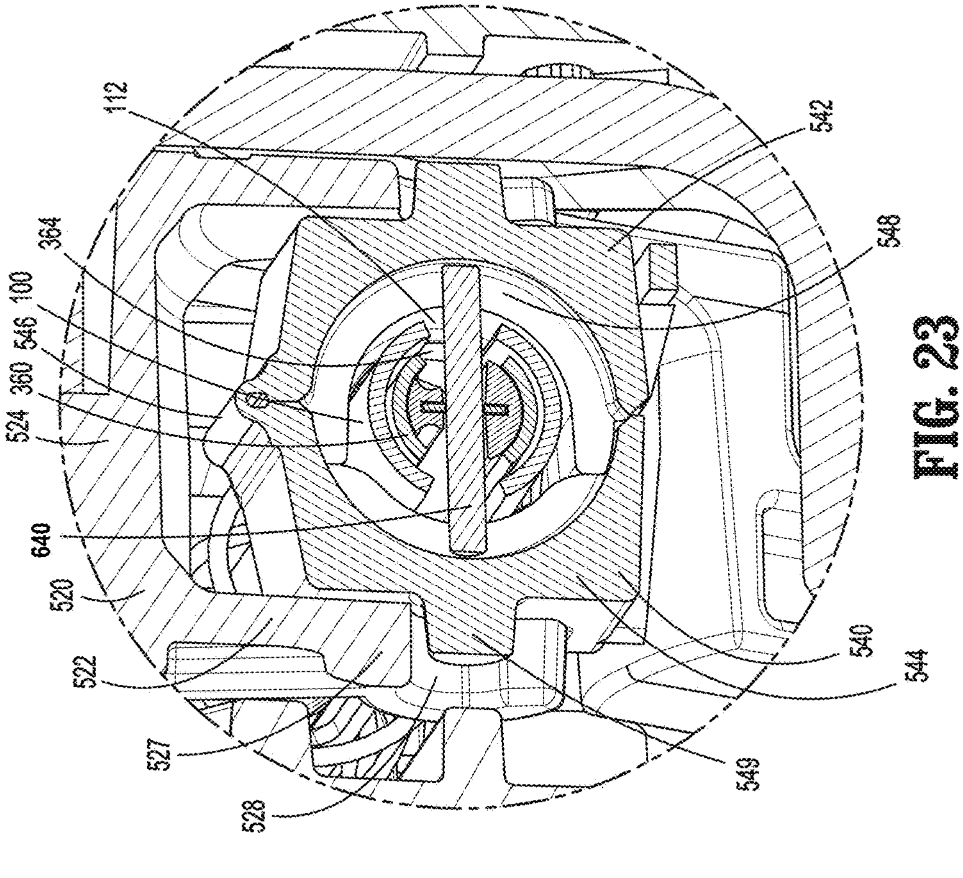
FIG. 23 is an enlarged view of the area of detail indicated as "23" in FIG. 22.
Figure 25:
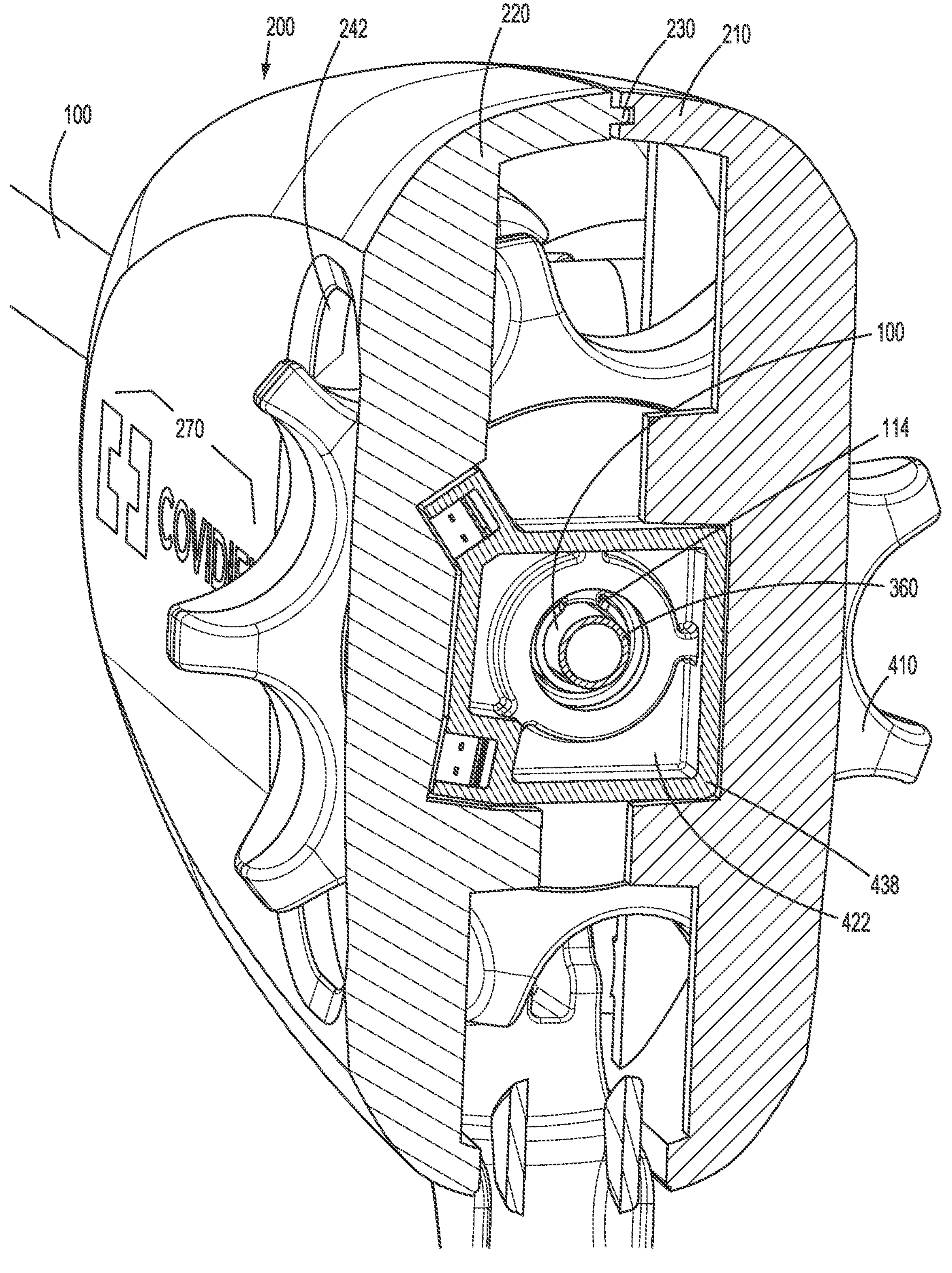
FIG. 25 is a transverse, cross-sectional view taken across section line "25-25" of FIG. 3.
Figure 26:
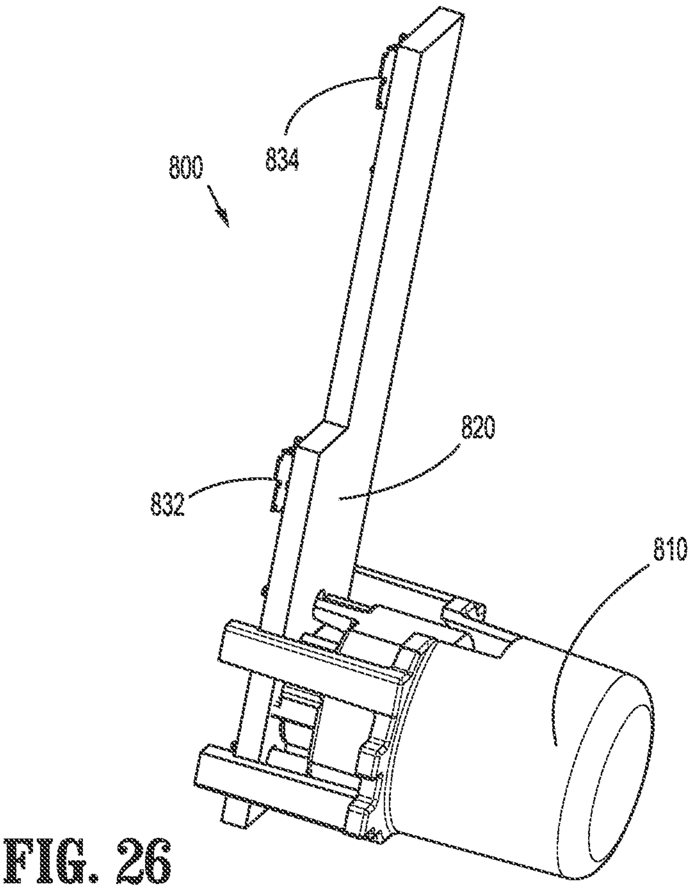
FIG. 26 is an enlarged view of the area of detail indicated as "26" in FIG. 4, providing a front perspective view of an activation assembly of the instrument of FIG. 1.
Figure 27:
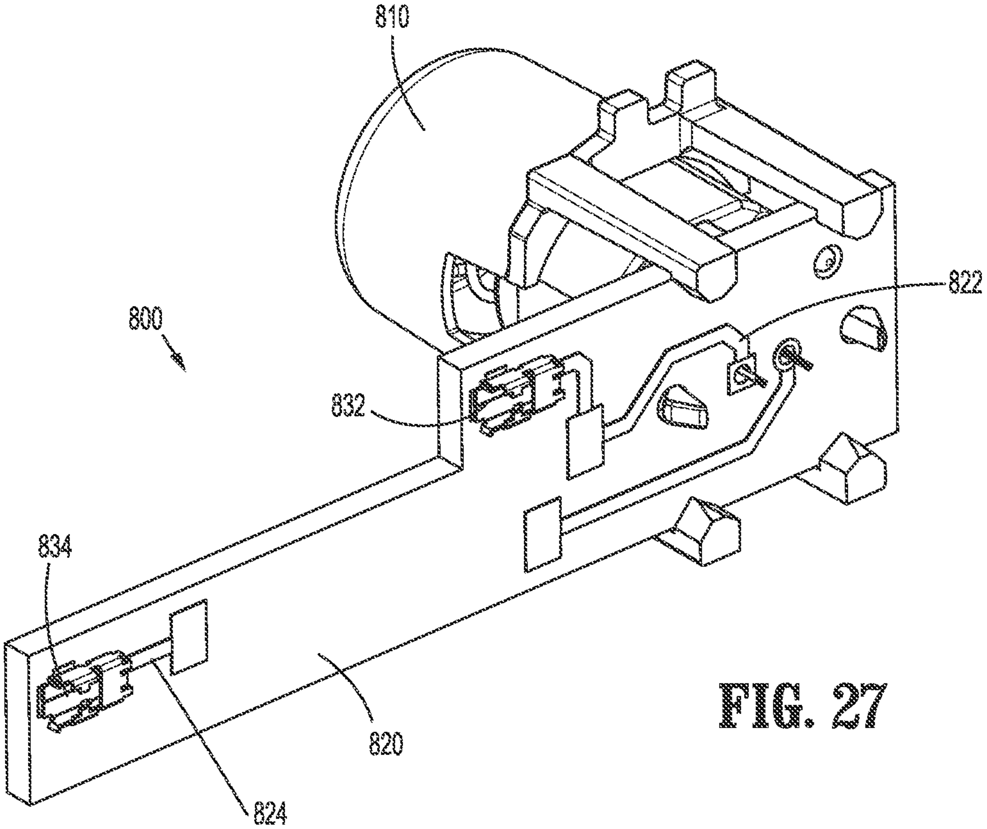
FIG. 27 is a rear, perspective view of the activation assembly of FIG. 26.

In other configurations of rotation assembly 400, first and second spring contacts 432, 434 can either or both be exchanged with another spring contact provided in accordance with the present disclosure: spring contact 450 shown in FIG. 20A. Referring to FIG. 20A, in conjunction with FIGS. 18-20, spring contact 450 includes a substructure 451 that extends from a first end portion 453 where substructure 451 defines a brush holder 452 to a second end portion 459 where substructure 451 defines an extension 457. Spring contact 450 is configured to be fixedly secured to body 422 and, thus housing 200 (see also FIGS. 21-25), at least via receipt of an electrical connector 458 of spring contact 450 within connector slot 448, similarly as detailed above with respect to spring contacts 432, 434. Electrical connector 458 is transversely disposed on the second end portion 459 of the substructure 451, such that the proximal face of electrical connector 458 extends beyond the width of substructure 451 to define a protruding end which is inserted through the connector slots 448. Electrical connector 458 is configured to slide and lock into engagement and electrical coupling with one of the lead connectors 912 or 922 of lead wires 910 or 920 e.g., as male-female connectors detailed above.

Spring contact 450 is biased into contact with at least one of inner or outer contact rings 432, 434 by a spring 456 and a brush 454 that has electrically conductive properties, e.g., a carbon graphite brush. Spring 456 is disposed within the brush holder 452 and is positioned between a bracer 461 defined by the substructure 451 at one end and brush 454 at the other end. Brush 454 is partially inserted into brush holder 452 such that brush 454 can slide farther into or outwardly from the brush holder 452 against the bias of spring 456 or with the bias of spring 456, respectively. Spring 456 is at least partially compressed between the brush 454 and the bracer 461 of substructure 451 such that spring 456 continuously exerts a biasing force against brush 454 to ensure that brush 454 constantly maintains contact with at least one of inner or outer contact rings 424, 426, even if brush 454 wears down to a shorter length after prolonged use. Further, this arrangement ensures that spring contact 450 maintains contact with at least one of inner or outer contact rings 424, 426, regardless of the rotational orientation of rotation wheel 410 relative to body 422, thus maintaining electrical connection and permitting continuous, e.g., infinite, rotation of rotation wheel 410 in either direction relative to body 422 and housing 200. In aspects, a wire 455, e.g., a copper wire, is coupled to brush 454 and placed in contact with some portion of substructure 451 to electrically connect brush 454 and electrical connector 458 with one another.

Figure 34:
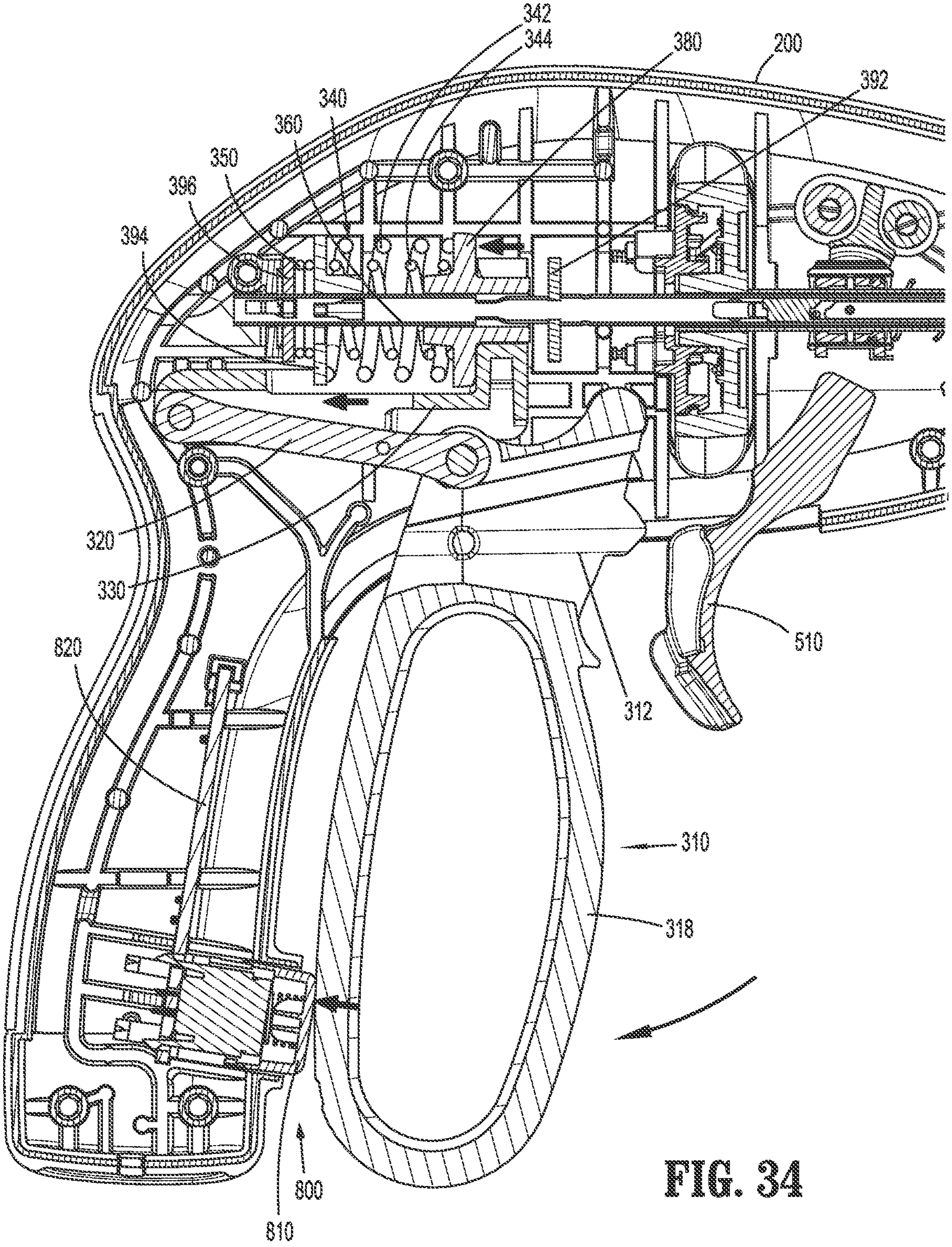
FIG. 34 is a longitudinal, cross-sectional view of a proximal portion of the instrument of FIG. 1 illustrating the movable handle in an activated position activating the activation assembly.
Figure 35:
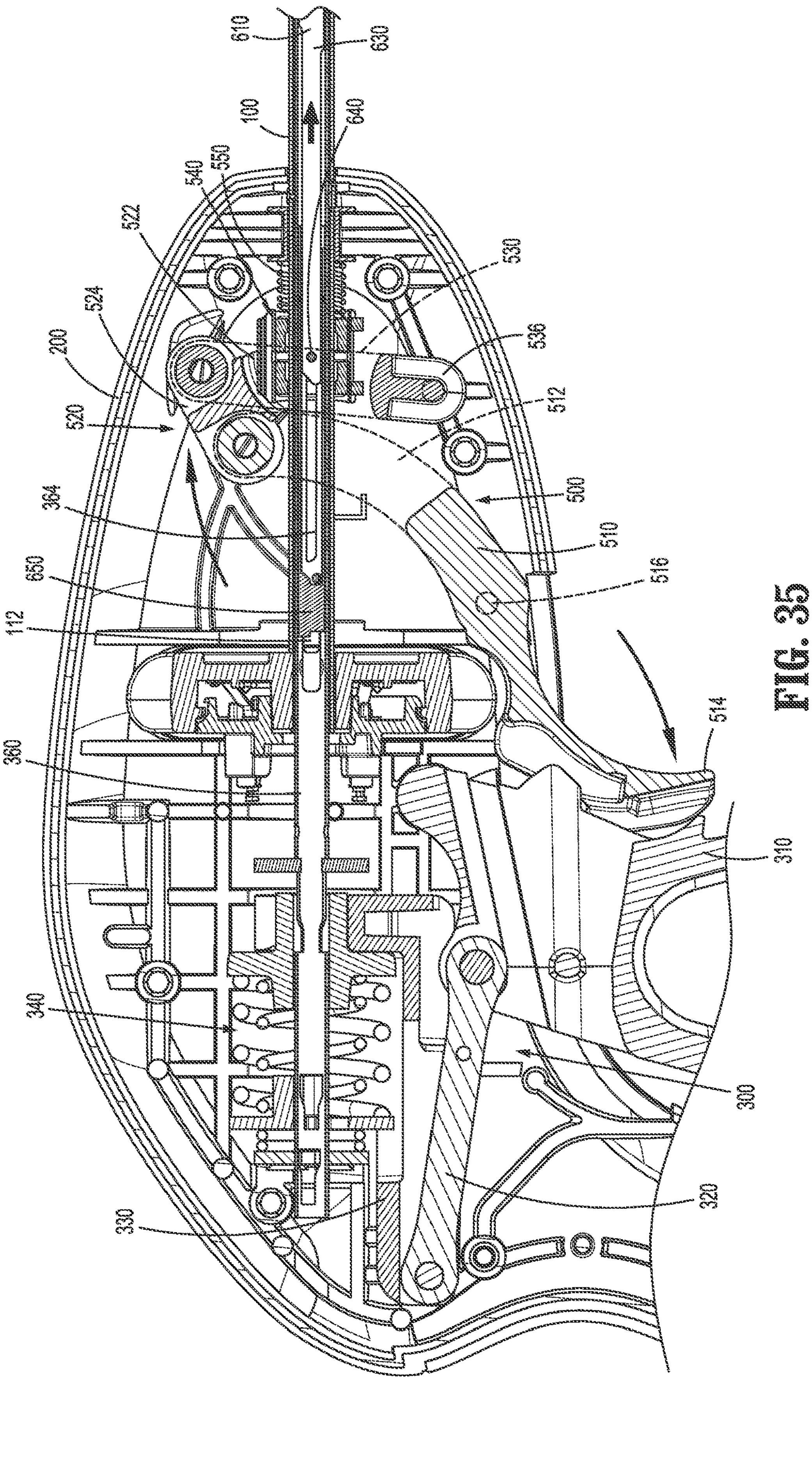
FIG. 35 is a longitudinal, cross-sectional view of a proximal portion of the instrument of FIG. 1 illustrating actuation of a trigger of the trigger assembly to deploy the knife assembly.

Referring to FIGS. 1, 4, 26, 27, 31, and 34, activation assembly 800 is disposed within fixed handle portion 290 of housing 200 and includes an activation button 810 and a circuit board 820. Activation button 810 protrudes distally through activation button aperture 236 of housing 200 while circuit board 820 is retained within board support 238 of housing 200. Activation button 810 includes an internal electrical switch and is mounted on circuit board 820 such that the electrical switch thereof is in selective electrical communication with electrical trace 822 of circuit board 820. As detailed above, movable handle 310 is pivotable relative to housing 200 between the un-actuated position (FIG. 28), the actuated position (FIG. 31), and the activation position (FIG. 34). In the activation position, grasping portion 318 of movable handle 310 is urged into contact with the exposed portion of activation button 810 to activate activation button 810 of activation assembly 800, e.g., to establish or break electrical connection via the switch of activation button 810.

Electrical trace 822 extends along circuit board 820 from activation button 810 to connectors 832 disposed on circuit board 820. Another electrical trace 824 is connected to connector 834 on circuit board 820. Connectors 832, 834 may be male or female slide connectors, similarly as detailed above, configured to electrical couple with lead wires 910, 920 (FIG. 19), respectively. Circuit board 820 further includes plural contacts to which the wires of cable 900 are attached, e.g., soldered, to thereby electrically couple circuit board 820 with the energy source, e.g., an electrosurgical generator (not shown), via plug 940 of cable 900 (see FIG. 1), and to thereby selectively electrically couple lead wires 910, 920 (FIG. 19) with the energy source.

The establishment or breaking of electrical connection via the switch of activation button 910, e.g., as a result of the depression of activation button 810 by movable handle 310 to activation the switch of activation button 810, can be detected at the generator via monitoring at least one of the wires connected, e.g., soldered, to circuit board 820. Thus, the generator can readily determine when activation button 810 has been activated and, in response thereto, initiate the supply of energy through wires of cable 900 to circuit board 820 and, thus, to lead wires 910, 920 (FIG. 19) to energize electrically-conductive plates 750, 790 of jaw members 720, 760, respectively, for treating tissue grasped therebetween.

With reference to FIGS. 37-41, another energy-based surgical instrument provided in accordance with the present disclosure and configured for grasping, treating, and/or dividing tissue is shown generally identified by reference numeral 1010. Instrument 1010 is similar to instrument 10 (FIG. 1) and may include any of the features thereof except as explicitly contradicted below. Accordingly, only differences between instrument 1010 and instrument 10 (FIG. 1) are detailed below.

Instrument 1010 includes a latching mechanism 1020 configured to lock movable handle 1310 in the actuated positon, thereby latching the jaw members thereof (not shown, the same as jaw members 720, 760 of instrument 10 (FIG. 1)) in the approximated position. Further, activation assembly 1800 of instrument 1010 is relocated to the rear of body portion 1280 of housing 1200 to enable selective activation by a finger of a user rather than by movable handle 1310, although other positions and/or configurations of activation assembly 1800 are also contemplated.

Latching mechanism 1020 of instrument 1010 includes a latch arm 1030 coupled to movable handle 1310 and a latch track 1050 disposed within, e.g., defined within one (or both) of the housing parts 1210, 1220 of housing 1200, although the reverse configuration is also contemplated. Latch arm 1030 is monolithically formed as a single piece, e.g., via molding, and includes an engagement hook 1032 defined at a first end portion thereof and a transverse latch post 1034 protruding from one (or both) sides of latch arm 1030 at a second, opposite end portion thereof. Latch arm 1030 is flexible, enabling deflection of transverse latch post 1034 relative to engagement hook 1032 about at least two axes.

Engagement hook 1032 of latch arm 1030 defines a notch 1036 and a mouth 1038 providing access to notch 1036. Notch 1036 is circumferentially surrounded by engagement hook 1032 about at least 270 degrees of a circumference of notch 1036. Engagement hook 1032 is configured for snap-fit engagement about a latch boss 1319 of movable handle 1310 with latch boss 1319 passing through mouth 1038 and into engagement within notch 1036 wherein engagement hook 1032 provides at least 270 degrees of retention about latch boss 1319. Thus, engagement hook 1032 can be readily engaged and maintained in engagement about latch boss 1319. Latch boss 1319 may be monolithically formed with movable handle 1310.

Latch track 1050 of latching mechanism 1020 defines a tortuous path about a central block 1052, an upper guide rail 1054, a lower guide rail 1056, and a rear guide leg 1058. Latch track 1050, more specifically, includes an entry path 1062 defined between central block 1052 and lower guide rail 1056, a latching path 1064 defined around central block 1052 between lower guide rail 1056 and rear guide leg 1058 and interconnecting entry path 1062 with a saddle 1066 defined within central block 1052, an unlatching path 1068 defined around central block 1052 between rear guide leg 1058 and upper guide rail 1054 and interconnecting saddle 1066 with a return path 1070, and return path 1070 defined between central block 1052 and upper guide rail 1054. Return path 1070 includes a transverse ramp 1080 that, as detailed below, includes a proximal ramped end 1082 and a distal cliff end 1084.

Referring still to FIGS. 37-41, in use, upon pivoting of movable handle 1310 from the un-actuated position towards the actuated position, transverse latch post 1034 is moved proximally towards latch track 1050. Upon further pivoting of movable handle 1310 towards the actuated position, transverse latch post 1034 enters entry path 1062 and travels distally therethrough between central block 1052 and lower guide rail 1056. Latch arm 1030 is deflected, e.g., about a first axis, downwardly to enable transverse latch post 1034 to travel through entry path 1062. Further, excursion of transverse latch post 1034 into return path 1070 is inhibited by distal cliff end 1084; that is, transverse latch post 1034 is inhibited from climbing distal cliff end 1084 and, thus, is inhibited from entering return path 1070, thereby ensuring that transverse latch post 1034 correctly follows entry path 1062.

Movable handle 1310 is further pivoted proximally to and beyond the actuated position to an over-actuated position to enable transverse latch post 1034 to clear central block 1052. Once transverse latch post 1034 clears central block 1052 and, thus, latch arm 1030 is no longer held in a deflected position thereby, latch arm 1030 is resiliently returned upwardly such that transverse latch post 1034 is urged towards or into contact with rear guide leg 1058. This may be confirmed by audible and/or tactile feedback.

Figure 2:
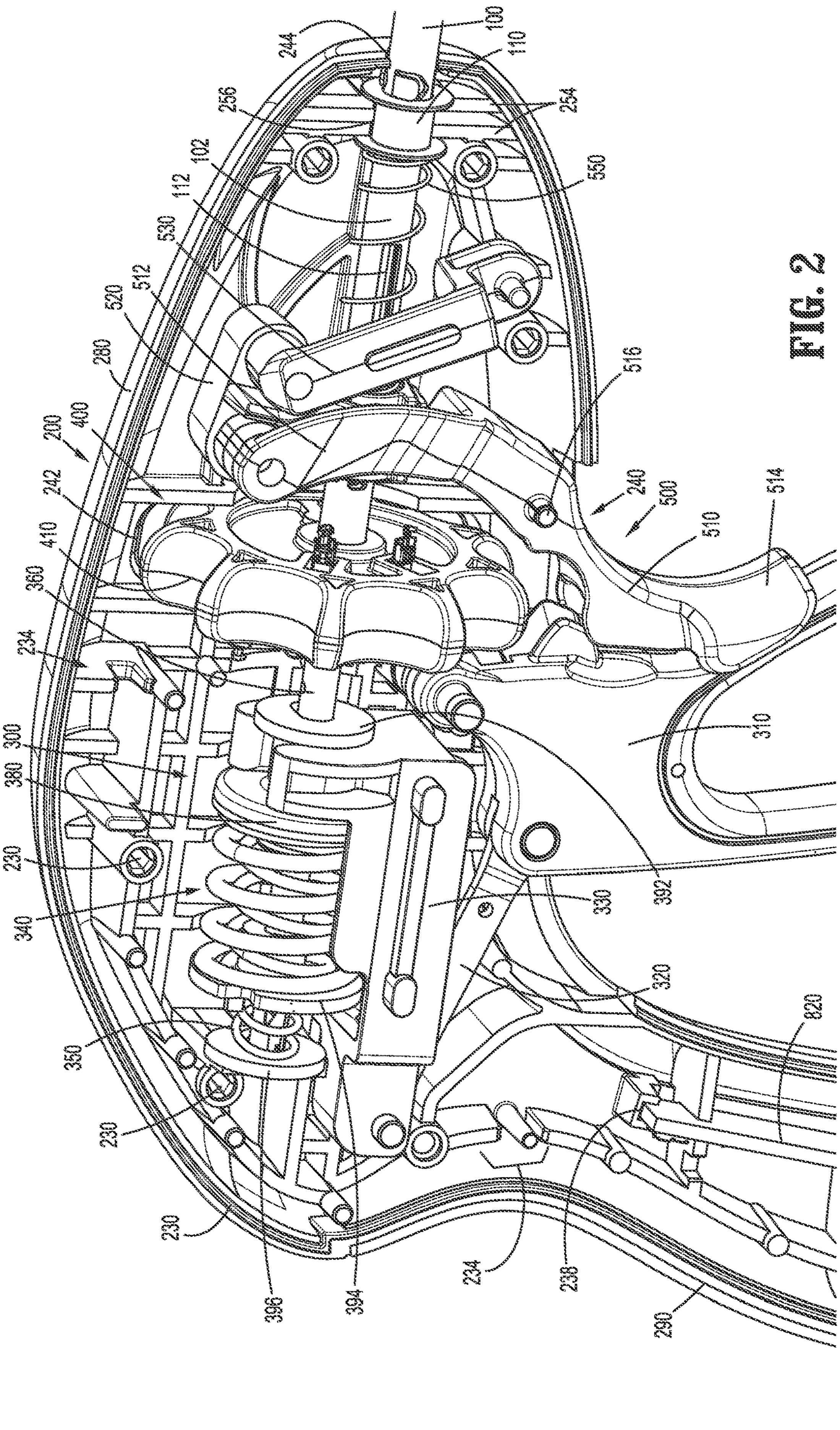
FIG. 2 is a first side perspective view of a proximal portion of the instrument of FIG. 1 with a portion of the housing removed to illustrate internal features therein.
Figure 3:
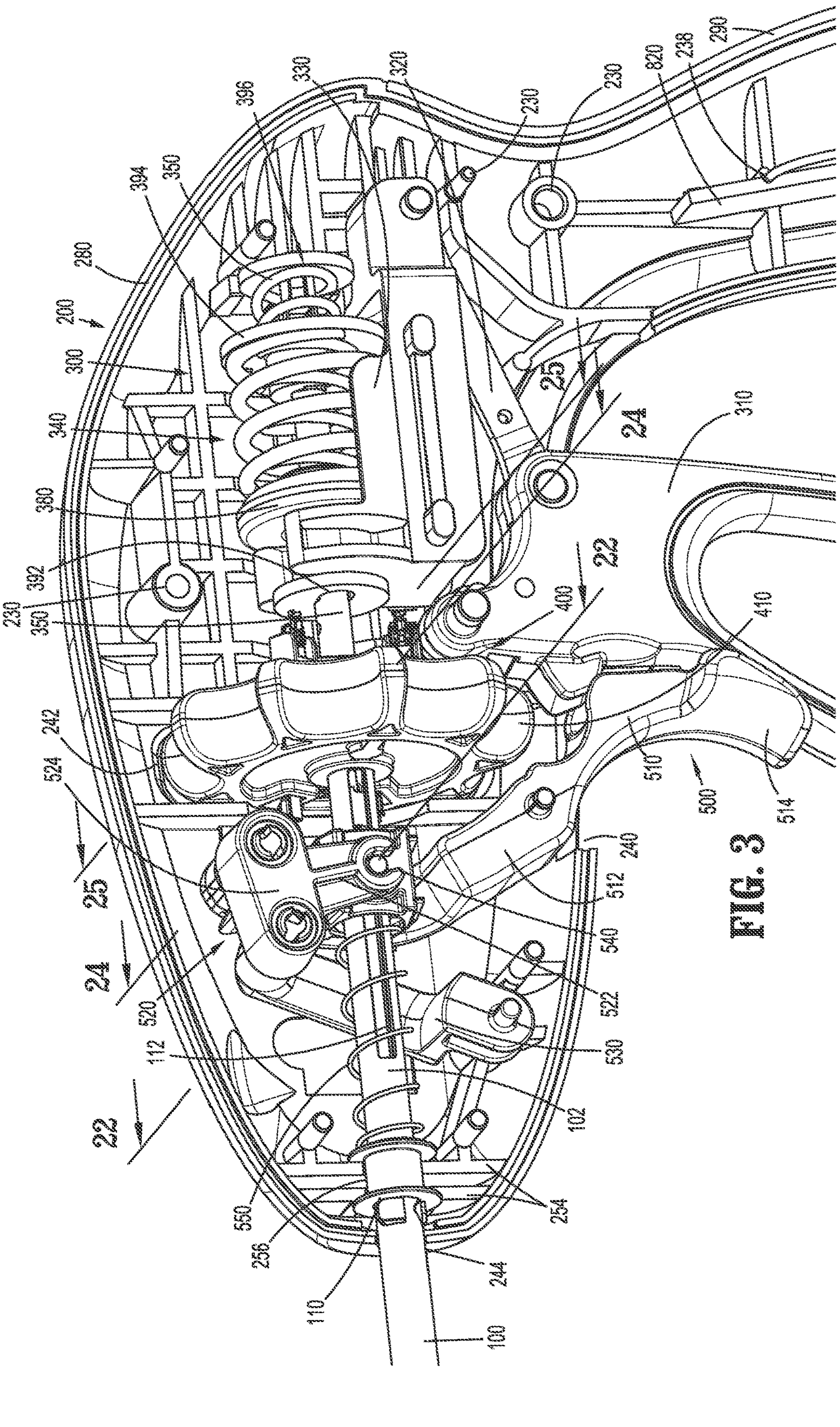
FIG. 3 is a second, opposite side perspective view of the proximal portion of FIG. 2 with a portion of the housing removed to illustrate internal features therein.
Figure 4:
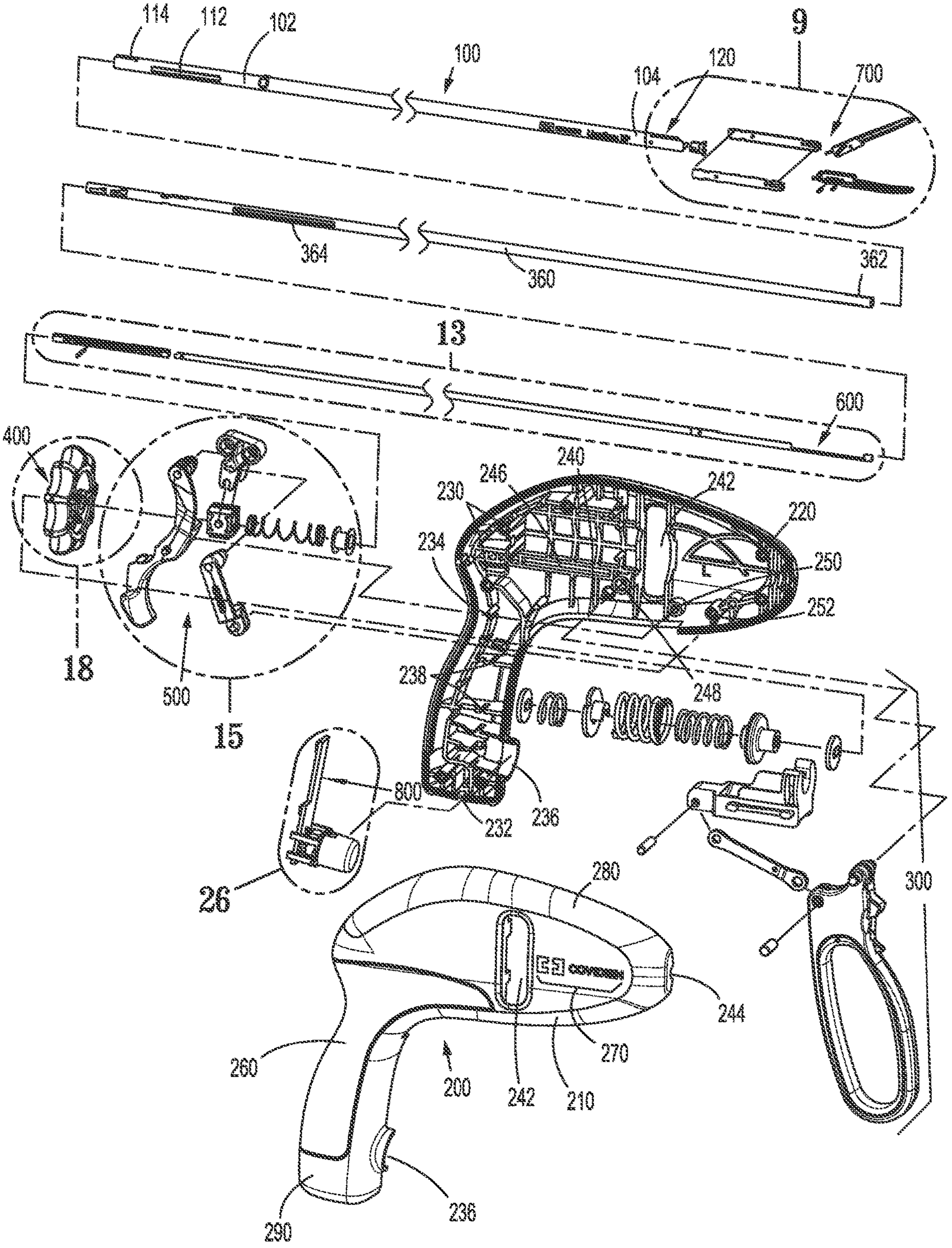
FIG. 4 is an exploded, perspective view of the instrument of FIG. 1.
Figure 5:
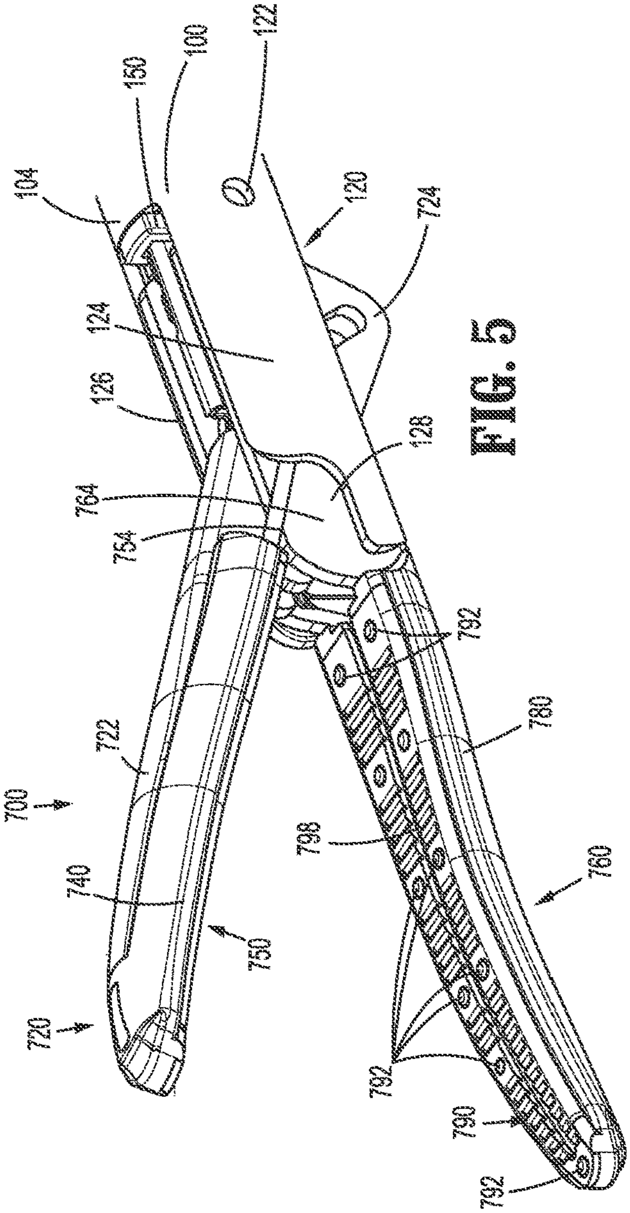
FIG. 5 is an enlarged view of the area of detail indicated as "5" in FIG. 1 illustrating a distal portion of the instrument of FIG. 1.

Once movable handle 1310 reaches the over-actuated position, movable handle 1310 may be released (or returned), allowing movable handle 1310 to return distally back towards the actuated position under the bias of the return spring (not shown, the same as return spring 350 (FIGS. 2 and 3). Upon release (or return) of movable handle 1310, transverse latch post 1034 is moved distally through latching path 1064 and into saddle 1066 defined within central block 1052, thereby latching movable handle 1310 in the actuated position. With movable handle 1310 latched in the actuated position, the jaw members of instrument 1010 are correspondingly locked in the approximated position applying an appropriate jaw force to tissue grasped therebetween such that the jaw members may be energized to treat, e.g., seal, tissue grasped therebetween.

In order to release movable handle 1310 from the latched condition and enable return of the jaw members to the spaced-apart position, e.g., after tissue treatment and/or cutting, or to re-grasp tissue, movable handle 1310 is again pivoted proximally from the actuated position to the over-actuated position. When movable handle 1310 is pivoted to the over-actuated position, transverse latch post 1034 is moved proximally from saddle 1066 through the unlatching path 1068 to clear central block 1052, thus allowing latch arm 1030 to further resiliently return upwardly such that transverse latch post 1034 is urged towards or into contact with upper guide rail 1054.

Once movable handle 1310 reaches the over-actuated position, movable handle 1310 may be released (or returned), allowing movable handle 1310 to return distally. This distal return of movable handle 1310 pulls transverse latch post 1034 distally through return path 1070, between upper guide rail 1054 and central block 1052. As transverse latch post 1034 is moved distally through return path 1070, transverse latch post 1034 ramps over proximal ramped end 1082 of transverse ramp 1080 and along transverse ramp 1080, thereby increasingly deflecting latch arm 1030 transversely (e.g., about a second axis) until transverse latch post 1034 falls off distal cliff end 1084 of transverse ramp 1080, allowing latch arm 1030 to resiliently return transversely. After transverse latch post 1034 falls off distal cliff end 1084 of transverse ramp 1080, proximal return of transverse latch post 1034 through return path 1070 is inhibited and, thus, re-actuation of movable handle 1310 thereafter moves transverse latch post 1034 along entry path 1062. In the absence of re-actuation of movable handle 1310, movable handle 1310 continues to return distally towards the un-actuated position, allowing transverse latch post 1034 to clear latch track 1050 and allowing latch arm 1030 to return to its initial position corresponding to the un-actuated position of movable handle 1310.

While several configurations of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular configurations. Those skilled in the art will envision other modifications within the scope and spirit of the claims appended hereto.

What is claimed is:

1. A rotation assembly for a surgical instrument, comprising:

a first body and a second body, one of the first body or the second body fixedly disposed within a housing of the surgical instrument and defining a central bore configured to rotatably receive a shaft of the surgical instrument, the other of the first body or second body rotatably disposed within the housing and fixedly disposed about the shaft, wherein the shaft extends distally from and is rotatable relative to the housing;

an inner contact ring fixedly disposed on the first body and including a first electrical connector coupled thereto; and an outer contact ring fixedly disposed on the first body and including a second electrical connector coupled thereto, the outer contact ring electrically isolated from the inner contact ring;

a first spring contact and a second spring contact configured to maintain electrical contact with the inner contact ring and the outer contact ring, respectively, wherein each of the first spring contact and the second spring contact includes:

a substructure including a brush holder positioned towards a first end portion thereof and an extension positioned towards a second end portion thereof;

an electrical connector disposed on the extension;

a brush slidably disposed partially within the brush holder, the brush including a contact portion extending from the brush holder and configured to establish electrical contact with the inner or outer contact ring; and a spring disposed at least partially within the brush holder and configured to bias the brush towards the inner or outer contact ring to maintain electrical contact therebetween.

2. The rotation assembly according to claim 1, wherein the first body is a continuous rotation assembly and the second body is a rotation wheel of the surgical instrument.

3. The rotation assembly according to claim 1, further including a disc disposed within the first body, the disc including: a proximal face, a distal face, and an outer rim.

4. The rotation assembly according to claim 3, wherein the distal face is recessed relative to the outer rim.

5. The rotation assembly according to claim 3, wherein the outer rim is configured for rotatable receipt within a recessed portion of the second body, such that a cavity is formed between the distal face of the disc and the recessed portion of the second body.

6. The rotation assembly according to claim 5, wherein both the inner contact ring and the outer contact ring are disposed within the cavity.

7. The rotation assembly according to claim 6, wherein the inner contact ring disposed within the cavity is fixed relative to the recessed portion of the second body and fixed relative to the first electrical connector.

8. The rotation assembly according to claim 6, wherein the outer contact ring disposed within the cavity is fixed relative to the recessed portion of the second body and fixed relative to the second electrical connector.

9. The rotation assembly according to claim 3, further including a frame defined on the distal face of the disc to surround the central bore and configured to be fixedly captured within the housing.

10. The rotation assembly according to claim 1, wherein the second body is configured to rotate the shaft into a desired orientation, relative to the housing.

11. The rotation assembly according to claim 1, wherein the second body is rotatable continuously in either direction without limitation.

12. The rotation assembly according to claim 1, wherein the second body includes a plurality of flutes arranged annularly about an annular periphery thereof.

13. The rotation assembly according to claim 1, wherein the brush is a carbon graphite brush.

14. The rotation assembly according to claim 1, further including a proximal facing pair of connector slots disposed in the second body, the proximal facing pair of connector slots configured to receive the first electrical connector and the second electrical connector.

15. The rotation assembly according to claim 1, further including a distal facing pair of connector slots disposed in the first body, the distal facing pair of connector slots configured to receive a pair of a third electrical connector and a fourth electrical connector.

16. A surgical instrument, comprising:

a housing;

an end effector assembly distally-spaced from the housing;

a movable handle operably coupled to the housing and movable relative thereto between an un-actuated position and an actuated position;

a drive assembly operably coupled between the movable handle and the end effector assembly and configured such that movement of the movable handle from the un-actuated position to the actuated position manipulates the end effector assembly; and a rotation assembly including:

a first body and a second body, one of the first body or the second body fixedly disposed within a housing of a surgical instrument and defining a central bore configured to rotatably receive a shaft of the surgical instrument, the other of the first body or the second body rotatably disposed within the housing and fixedly disposed about the shaft, wherein the shaft extends distally from and is rotatable relative to the housing;

an inner contact ring fixedly disposed on the first body and including a first electrical connector coupled thereto; and an outer contact ring fixedly disposed on the first body and including a second electrical connector coupled thereto, the outer contact ring electrically isolated from the inner contact ring;

a first spring contact and a second spring contact configured to maintain electrical contact with the inner contact ring and the outer contact ring, respectively, wherein each of the first spring contact and the second spring contact includes:

a substructure including a brush holder positioned towards a first end portion thereof and an extension positioned towards a second end portion thereof;

an electrical connector disposed on the extension;

a brush slidably disposed partially within the brush holder, the brush including a contact portion extending from the brush holder and configured to establish electrical contact with the inner or outer contact ring; and a spring disposed at least partially within the brush holder and configured to bias the brush towards the inner or outer contact ring to maintain electrical contact therebetween.

* * * * *